(12) United States Patent
Yang et al.

(10) Patent No.: US 8,143,276 B2
(45) Date of Patent: Mar. 27, 2012

(54) 4-THIO SUBSTITUTED QUINOLINE AND NAPHTHYRIDINE COMPOUNDS

(75) Inventors: Zhen Yang, Ridgewood, NJ (US); Reza Fathi, Ho Ho Kus, NJ (US); Qiang Zhu, Edson, NJ (US); Hyun-Joon Cho, Spring Valley, NY (US); Yixin Liu, Paramus, NJ (US); Anthony Sandrasagra, Princeton, NJ (US); C. Richard Wobbe, Lexington, MA (US)

(73) Assignee: XTL Biopharmaceuticals Ltd., Rehovot (IL)

( * ) Notice: Subject to any disclaimer, the term of this patent is extended or adjusted under 35 U.S.C. 154(b) by 1017 days.

(21) Appl. No.: 11/895,088

(22) Filed: Aug. 22, 2007

(65) Prior Publication Data

US 2009/0054477 A1 Feb. 26, 2009

(51) Int. Cl.
*C07D 215/38* (2006.01)
*A61K 31/04* (2006.01)

(52) U.S. Cl. ....................... 514/312; 546/155
(58) Field of Classification Search .................. 546/155; 514/312
See application file for complete search history.

(56) References Cited

U.S. PATENT DOCUMENTS 6,015,820 A 1/2000 Bisagni et al.

FOREIGN PATENT DOCUMENTS

WO WO 2005/012288 A1 2/2005

OTHER PUBLICATIONS

Ismail, Mostafa, Molecules, VOl 5, pp. 1224-1239, 2000.*
Mirek, CA100:34434, abstract only of Polish J of Pharm and Pnarm, VOl 36(2), pp. 139-149, 1983.*
Mohamed, CA 122:31293, abstract only of J of Serbian Chem Soc, vol. 58(10), pp. 737-743, 1993.*
European Extended Search Report, European Application No. 07837234.9, Nov. 26, 2010, 7 pages.
Ismail, M.M. et al., "Chemistry Substituted Quinolinones. Part IV. Synthesis and Nucleophilic Reactions of 4-Chloro-8-Methylquinolin-2(1H)-One and Its Thione Analogue," Molecules, Molecular Diversity Preservation International, Basel, CH, 2000, pp. 1224-1239, vol. 5, No. 12.
Mirek, J. et al., "Synthesis and Pharmacological Properties of Some 7H-[1] Benzothiopyrano-[3,2-c] Quinolin-7-ones," Pol. J. Pharmacol. Pharm., 1983, pp. 139-149, vol. 35.
Mohamed, E-H. A. et al., "Synthesis and Behaviour of 2,4-Dichloro-6-Methylquinoline and 4-Chloro-6-Methyl-2(1H)Quinolone Towards Some Nucleophilic Reagents," Journal of the Serbian Chemical Society, Belgrade, YU, 1993, pp. 737-743, vol. 58, No. 10.

* cited by examiner

*Primary Examiner* — D M Seaman
(74) *Attorney, Agent, or Firm* — Fenwick & West LLP

(57) ABSTRACT

The present invention relates to 4-thio substituted quinoline and naphthyridine derivatives and processes for their preparation. The invention also related to methods for treating infection of Hepatitis C virus by administering a 4-thio substituted quinoline or naphthyridine derivative.

18 Claims, No Drawings

4-THIO SUBSTITUTED QUINOLINE AND NAPHTHYRIDINE COMPOUNDS

FIELD OF THE INVENTION

The present invention relates to 4-thio substituted quinoline and naphthyridine derivatives and processes for their preparation. The invention also relates to methods for treating infection of Hepatitis C virus by administering a 4-thio substituted quinoline or naphthyridine derivative. The invention provides a synthetic process for the preparation of 4-thio substituted quinoline and naphthyridine derivatives using mild reaction conditions, which provides a high substituent tolerance and is appropriate for use in solid phase syntheses for producing a library of 4-thio substituted quinoline and naphthyridine derivatives for biological screening.

BACKGROUND OF THE INVENTION

Infection with the Hepatitis C virus (HCV) represents a serious world-wide health crisis. In more than 70% of infected individuals, the virus evades clearance by the immune system leading to a persistent HCV infection. The long term effects of persistent HCV infection range from an apparently healthy carrier state to chronic hepatitis, liver fibrosis, cirrhosis, and eventually hepatocellular carcinoma. HCV is a leading cause of chronic liver disease. A leading therapy currently available for treatment of HCV infection uses a combination of pegylated α-interferon and ribavirin. However, many of the patients treated with this therapy fail to show a sufficient antiviral response. Additionally, interferon treatment also induces severe side-effects (i.e. retinopathy, thyroiditis, acute pancreatitis, depression) that diminish the quality of life of treated patients. Thus, it is important that more effective treatments be identified.

The identification of inhibitors of HCV replication and/or proliferation has been facilitated by the development of a cell-based system to study HCV replication. Inhibition of HCV replication may be performed using the HCV Replicon Assay developed in the laboratories of Bartenschlager (Lohman et al, Science 285, 110-113, 1999) and Rice (Blight et al, Science 290, 1972-1974, 2000). The assay is performed using the Huh-Luc-Neo cell line (Lohman et al, Science 285, 110-113, 1999). Huh-Luc-Neo cells are a human hepatoma cell line (Huh-7) stably expressing a bi-cistronic subgenomic replicon containing the HCV IRES in which the structural proteins of HCV have been deleted and replaced by a construct containing sequences coding for the firefly luciferase reporter gene, the neomycin selectable marker and the EMCV IRES to direct expression of a truncated HCV genome expressing the structural proteins NS3, NS4A, NS4B, NS5A, and NS5B. HCV targets through which inhibitors could act to inhibit replication include the NS3 protease, the helicase/ATPase, NS5A, the NS5B-RNA dependent RNA polymerase, and the HCV IRES.

Strategies in new drug discovery often look to natural products for leads in finding new chemical compounds with therapeutic properties. One of the recurring problems in drug discovery is the availability of organic compounds derived from natural sources. Techniques employing combinatorial chemistry attempt to overcome this problem by allowing the high throughput synthesis and testing of hundreds or thousands of related synthetic compounds, called a chemical library. In designing the synthesis of a prospective therapeutic compound or a chemical library, one often looks to natural chemical motifs which are known to have broad biological activity. Quinoline derivatives are of particular interest due to their frequent occurrence in nature and range of biological activities.

Derivatives of both quinoline and naphthyridine possess a range of biological activities. To avoid confusion, the quinoline and naphthyridine derivatives described herein are numbered according to the following convention:

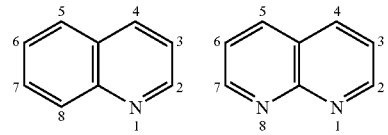

SUMMARY OF THE INVENTION

The present invention provides 4-thio substituted quinoline and naphthyridine derivatives having the formula I

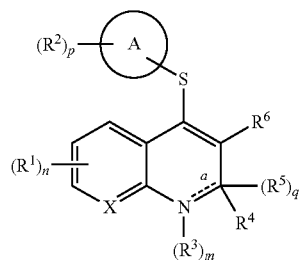

(I)

wherein:
a represents an optional double bond;
X is selected from N, C—H and C—$R^1$;
each $R^1$ is independently selected from alkyl, alkenyl, alkynyl, aralkyl, —$(CH_2)_r$—O—$R^{11}$, —$(CH_2)_r$—N($R^{12}$)($R^{13}$), $(CH_2)_r$—N($R^{11}$)—$(CH_2)_s$C(O)$R^{14}$, —$(CH_2)_r$—N($R^{11}$)$SO_2R^{11}$, —$(CH_2)_r$—SR$^{11}$, —$(CH_2)_r$—C(O)$R^{14}$, —$(CH_2)_r$—C(O)—$(CH_2)_s$OR$^{11}$, —$(CH_2)_r$—C(O)—$(CH_2)_s$N($R^{12}$)($R^{13}$), —$(CH_2)_r$—O—$(CH_2)_s$—C(O)$R^{14}$, —$(CH_2)_r$OC(O)—$(CH_2)_s$N($R^{12}$)($R^{13}$), CN, CF$_3$, NO$_2$, SO$_2$, —SOR$^{11}$, —SO$_3$R$^{11}$, —SO$_2$N($R^{12}$)($R^{13}$), cycloalkyl, cycloalkenyl, halo, phosphate, phosphonate, aryl and a heterocyclic group;
additionally or alternatively two $R^1$ substituents on adjacent ring atoms may be combined to form a fused 5 or 6-membered ring, wherein the fused 5- or 6-membered ring may contain from 0 to 3 ring heteroatoms and may be further substituted with one or more substituents selected from $R^{11}$;
each $R^{11}$ is independently selected from H, alkyl, alkyl-O-alkyl, alkyl-O-aryl, alkenyl, alkynyl, cycloalkyl, cycloalkenyl, aralkyl, aryl and a heterocyclic group;
each $R^{12}$ and $R^{13}$ are independently selected from H, alkyl, cycloalkyl, cycloalkenyl, alkyl-O-alkyl, alkyl-O-aryl, alkenyl, alkynyl, aralkyl, aryl and a heterocyclic group; or $R^{12}$ and $R^{13}$ may be taken together with the nitrogen to which they are attached form a 5- to 7-membered ring which may optionally contain a further heteroatom and may be optionally substituted with up to three substituents selected from halo, CN, NO$_2$, alkyl, cycloalkyl, alkenyl, alkynyl, aralkyl, aryl, and a heterocyclic group;

each $R^{14}$ is independently selected from H, alkyl, —OH, —O-alkyl, —O-aryl, —O-aralkyl, -alkyl-O-alkyl, -alkyl-O-aryl, alkenyl, alkynyl, cycloalkyl, cycloalkenyl, aralkyl, aryl and a heterocyclic group;
r is 0 to 6;
s is 0 to 6;
n is 0 to 3;
A is a 5-, or 6-membered ring optionally comprising 0 to 3 heteroatoms;
each $R^2$ is selected from the group consisting of alkyl, alkenyl, alkynyl, aralkyl, —$(CH_2)_v$—O—$R^{21}$, —$(CH_2)_v$—N$(R^{22})(R^{23})$, —$(CH_2)_v$—N$(R^{21})$—$(CH_2)_w$—C(O)$R^{24}$, —$(CH_2)_v$—N$(R^{21})SO_2R^{21}$, —$(CH_2)_v$—SR$^{21}$, —$(CH_2)_v$—C(O)R$^{24}$, —$(CH_2)_v$—C(O)—$(CH_2)_w$OR$^{21}$, —$(CH_2)_v$—C(O)$(CH_2)_w$—N$(R^{22})(R^{23})$, —$(CH_2)_v$—O—$(CH_2)_w$—C(O)R$^{24}$, —$(CH_2)_v$—OC(O)—$(CH_2)_w$—N$(R^{22})(R^{23})$, CN, CF$_3$, NO$_2$, SO$_2$, —SOR$^{21}$, —SO$_3R^{21}$, —SO$_2$N$(R^{22})(R^{23})$, —NH—C(S)—NH—$R^{21}$, cycloalkyl, cycloalkenyl, halo, phosphate, phosphonate, aryl and a heterocyclic group;
additionally or alternatively two $R^2$ substituents on adjacent ring atoms may be combined to form a fused 5 or 6-membered ring, wherein the fused 5- or 6-membered ring may contain from 0 to 3 ring heteroatoms and may be further substituted with one or more substituents selected from $R^{21}$;
each $R^{21}$ is independently selected from H, alkyl, alkyl-O-alkyl, alkyl-O-aryl, alkenyl, alkynyl, cycloalkyl, cycloalkenyl, aralkyl, aryl and a heterocyclic group;
each $R^{22}$ and $R^{23}$ are independently selected from H, alkyl, cycloalkyl, cycloalkenyl, alkyl-O-alkyl, alkyl-O-aryl, alkenyl, alkynyl, aralkyl, aryl and a heterocyclic group; or $R^{22}$ and $R^{23}$ may be taken together with the nitrogen to which they are attached form a 5- to 7-membered ring which may optionally contain a further heteroatom and may be optionally substituted with up to three substituents selected from halo, CN, NO$_2$, alkyl, cycloalkyl, alkenyl, alkynyl, aralkyl, aryl, and a heterocyclic group,
each $R^{24}$ is independently selected from H, alkyl, —OH, —O-alkyl, —O-aryl, —O-aralkyl, -alkyl-O-alkyl, -alkyl-O-aryl, alkenyl, alkynyl, cycloalkyl, cycloalkenyl, aralkyl, aryl and a heterocyclic group;
v is 0 to 6;
w is 0 to 6;
p is 0 to 3
$R^3$ is selected from the group consisting of H, alkyl, cycloalkyl, alkenyl, alkynyl, aralkyl, aryl, a heterocyclic group, —$(CH_2)_xC(O)R^{31}$, —$(CH_2)_xC(O)N(R^{32})(R^{33})$, $(CH_2)_xC(O)OR^{31}$,
$R^{31}$ is selected from H, alkyl, cycloalkyl, cycloalkenyl, alkenyl, alkynyl, aralkyl, aryl and a heterocyclic group;
$R^{32}$ and $R^{33}$ are independently selected from H, alkyl, cycloalkyl, cycloalkenyl, alkenyl, alkynyl, aralkyl, aryl and a heterocyclic group;
or $R^{32}$ and $R^{33}$ may be taken together with the nitrogen to which they are attached to form a 5- to 7-membered ring which may optionally contain a further heteroatom and may be optionally substituted with up to three substituents selected from halo, CN, NO$_2$, alkyl, cycloalkyl, alkenyl, alkynyl, aralkyl, aryl, and a heterocyclic group;
x is 0 to 6;
m is 0 or 1;
$R^4$ is selected from the group consisting of H, halo, alkyl, cycloalkyl, alkenyl, alkynyl, aralkyl, aryl, a heterocyclic group, —$(CH_2)_y$—O—$R^{41}$, —$(CH_2)_y$—N$(R^{42})(R^{43})$, —$(CH_2)_y$—N$(R^{41})$—$(CH_2)_z$—C(O)R$^{41}$, —$(CH_2)_y$—N$(R^{41})SO_2R^{41}$, —$(CH_2)_y$—SR$^{41}$, —$(CH_2)_y$—C(O)R$^{41}$, —$(CH_2)_y$—C(O)OR$^{41}$, —$(CH_2)_y$—C(O)$(CH_2)_z$—N$(R^{42})(R^{43})$, —$(CH_2)_y$—OC(O)R$^{41}$, and —$(CH_2)_y$—OC(O)—$(CH_2)_z$—N$(R^{42})(R^{43})$;
each $R^{41}$ is independently selected from H, alkyl, cycloalkyl, cycloalkenyl, alkenyl, alkynyl, aralkyl, aryl and a heterocyclic group;
$R^{42}$ and $R^{43}$ are independently selected from H, alkyl, cycloalkyl, cycloalkenyl, alkenyl, alkynyl, aralkyl, aryl and a heterocyclic group;
or $R^{42}$ and $R^{43}$ may be taken together with the nitrogen to which they are attached to form a 5- to 7-membered ring which may optionally contain a further heteroatom and may be optionally substituted with up to three substituents selected from halo, CN, NO$_2$, alkyl, cycloalkyl, alkenyl, alkynyl, aralkyl, aryl, and a heterocyclic group;
y is 0 to 6;
z is 0 to 6;
$R^5$ is H;
or $R^4$ and $R^5$ taken together are =O;
q is 0 or 1; and
$R^6$ is selected from H, halo, alkyl, cycloalkyl, alkenyl, alkynyl, aralkyl, aryl, and a heterocyclic group;
or a pharmaceutically acceptable salt or hydrate thereof.

The invention also provides a synthetic process for the preparation of compounds of the formula I. The process uses mild reaction conditions, which provides a high substituent tolerance. Thus, the process is applicable to the preparation of a wide variety of 4-thio substituted quinoline and naphthyridine derivatives with diverse substitution patterns. Additionally, the process is appropriate for use with combinatorial synthesis techniques. Thus, the process provides a method for producing a library of 4-thio substituted quinoline and naphthyridine derivatives for biological screening.

The invention also provides compositions and methods for the treatment of HCV by administering a compound of the present invention in a therapeutically effective amount.

DETAILED DESCRIPTION OF THE INVENTION

The term "halo" or "halogen" as used herein includes fluorine, chlorine, bromine and iodine.

The term "alkyl" as used herein contemplates substituted or unsubstituted, straight and branched chain alkyl radicals containing from one to fifteen carbon atoms. The term "lower alkyl" as used herein contemplates both straight and branched chain alkyl radicals containing from one to six carbon atoms and includes methyl, ethyl, propyl, isopropyl, butyl, isobutyl, tert-butyl, and the like. The alkyl group may be optionally substituted with one or more substituents selected from halo, CN, NO$_2$, CO$_2$R, C(O)R, —O—R, —N(R')(R''), —N(R)C(O)R, —N(R)SO$_2$R, —SR, —C(O)N(R')(R''), —OC(O)R, —OC(O)N(R')(R''), SO$_2$, —SOR, —SO$_3$R, —SO$_2$N(R')(R''), phosphate, phosphonate, substituted and unsubstituted cycloalkyl, and substituted and unsubstituted cycloalkenyl, wherein the substituted cycloalkyl and the substituted cycloalkenyl may be substituted with one or more of halo, CN, CF$_3$, CO$_2$R, C(O)R, C(O)NR$_2$, NR$_2$, NO$_2$, and OR.

The term "alkenyl" as used herein contemplates substituted or unsubstituted, straight and branched chain alkene radicals containing from two to 8 carbon atoms. An alkenyl group may be optionally substituted with one or more substituents selected from halo, CN, NO$_2$, CO$_2$R, C(O)R, —O—R, —N(R')(R''), —N(R)C(O)R, —N(R)SO$_2$R, —SR, —C(O)N(R')(R''), —OC(O)R, —OC(O)N(R')(R''), SO$_2$, —SOR, —SO₃R, —SO₂N(R')(R"), phosphate, phosphonate, substituted and unsubstituted cycloalkyl, substituted and unsubstituted cycloalkenyl, substituted and unsubstituted aryl and a substituted and unsubstituted heterocyclic group, wherein the substituted cycloalkyl, substituted cycloalkenyl, substituted aryl and substituted heterocyclic group may be substituted with one or more of halo, CN, CF₃, CO₂R, C(O)R, C(O)NR₂, NR₂, NO₂, and OR.

The term "alkynyl" as used herein contemplates substituted or unsubstituted, straight and branched carbon chain containing from two to 8 carbon atoms and having at least one carbon-carbon triple bond. The term alkynyl includes, for example ethynyl, 1-propynyl, 2-propynyl, 1-butynyl, 3-methyl-1-butynyl, and the like. An alkynyl group may be optionally substituted with one or more substituents selected from halo, CN, NO₂, CO₂R, C(O)R, —O—R, —N(R')(R"), —N(R)C(O)R, —N(R)SO₂R, —SR, —C(O)N(R')(R"), —OC(O)R, —OC(O)N(R')(R"), SO₂, —SOR, —SO₃R, —SO₂N(R')(R"), phosphate, phosphonate, substituted and unsubstituted cycloalkyl, substituted and unsubstituted cycloalkenyl, substituted and unsubstituted aryl and substituted and a unsubstituted heterocyclic group, wherein the substituted cycloalkyl, substituted cycloalkenyl, substituted aryl and substituted heterocyclic group, may be substituted with one or more of halo, CN, CF₃, CO₂R, C(O)R, C(O)NR₂, NR₂, NO₂, and OR.

The term "cycloalkyl" as used herein contemplates substituted or unsubstituted cyclic alkyl radicals containing form 3 to 7 carbon atoms and includes cyclopropyl, cyclopentyl, cyclohexyl, and the like. A cycloalkyl group may be optionally substituted with one or more substituents selected from halo, CN, NO₂, CO₂R, C(O)R, —O—R, —N(R')(R"), —N(R)C(O)R, —N(R)SO₂R, —SR, —C(O)N(R')(R"), —OC(O)R, —OC(O)N(R')(R"), SO₂, —SOR, —SO₃R, —SO₂N(R')(R"), phosphate, phosphonate, substituted and unsubstituted alkyl, substituted and unsubstituted cycloalkenyl, substituted and unsubstituted aryl and a substituted and unsubstituted heterocyclic group, wherein the substituted alkyl, substituted cycloalkenyl, substituted aryl and substituted heterocyclic group may be substituted with one or more of halo, CN, CF₃, CO₂R, C(O)R, C(O)NR₂, NR₂, NO₂, and OR.

The term "cycloalkenyl" as used herein contemplates substituted or unsubstituted cyclic alkenyl radicals containing form 5 to 7 carbon atoms in which has a double bond between two of the ring carbons and includes cyclopentenyl, cyclohexenyl, and the like. A cycloalkenyl group may be optionally substituted with one or more substituents selected from halo, CN, NO₂, CO₂R, C(O)R, —O—R, —N(R')(R"), —N(R)C(O)R, —N(R)SO₂R, —SR, —C(O)N(R')(R"), —OC(O)R, —OC(O)N(R')(R"), SO₂, —SOR, —SO₃R, —SO₂N(R')(R"), phosphate, phosphonate, substituted and unsubstituted alkyl, substituted and unsubstituted alkenyl, substituted and unsubstituted aryl and a substituted and unsubstituted heterocyclic group, wherein the substituted alkyl, substituted alkenyl, substituted aryl and substituted heterocyclic group may be substituted with one or more of halo, CN, CF₃, CO₂R, C(O)R, C(O)NR₂, NR₂, NO₂, and OR.

The term "aralkyl" as used herein contemplates a lower alkyl group which has as a substituent an aromatic group, which aromatic group may be substituted or unsubstituted. An aralkyl group may be optionally substituted with one or more substituents selected from halo, CN, NO₂, CO₂R, C(O)R, —O—R, —N(R')(R"), —N(R)C(O)R, —N(R)SO₂R, —SR, —C(O)N(R')(R"), —OC(O)R, —OC(O)N(R')(R"), SO₂, —SOR, —SO₃R, —SO₂N(R')(R"), phosphate, phosphonate, substituted and unsubstituted alkyl, substituted and unsubstituted alkenyl, substituted and unsubstituted cycloalkyl, substituted and unsubstituted cycloalkenyl, substituted and unsubstituted aryl and a substituted and unsubstituted heterocyclic group, wherein the substituted alkyl, substituted alkenyl, substituted cycloalkyl, substituted cycloalkenyl, substituted aryl and substituted heterocyclic group may be substituted with one or more of halo, CN, CF₃, CO₂R, C(O)R, C(O)NR₂, NR₂, NO₂, and OR.

The terms phosphate and phosphonate as used herein refer to the moieties having the following structures, respectively:

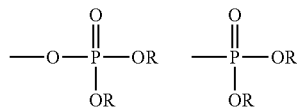

The term "heterocyclic group" or "heterocyclic ring" as used herein contemplates substituted or unsubstituted aromatic and non-aromatic cyclic radicals having at least one heteroatom as a ring member. Preferred heterocyclic groups are those containing 5 or 6 ring atoms which includes at least one hetero atom, and includes cyclic amines such as morpholino, piperidino, pyrrolidino, and the like, and cyclic ethers, such as tetrahydrofuran, tetrahydropyran, and the like. Aromatic heterocyclic groups, also termed "heteroaryl" groups contemplates single-ring hetero-aromatic groups that may include from one to three heteroatoms, for example, pyrrole, furan, thiophene, imidazole, oxazole, thiazole, triazole, pyrazole, pyridine, pyrazine, pyridazine, pyrimidine, and the like. The term heteroaryl also includes polycyclic hetero-aromatic systems having two or more rings in which two atoms are common to two adjoining rings (the rings are "fused") wherein at least one of the rings is a heteroaryl, e.g., the other rings can be cycloalkyls, cycloalkenyls, aryl, heterocycles and/or heteroaryls. Examples of polycyclic heteroaromatic systems include quinoline, isoquinoline, tetrahydroisoquinoline, quinoxaline, quinaxoline, benzimidazole, benzofuran, purine, imidazopyridine, benzotriazole, and the like. A heterocyclic group may be optionally substituted with one or more substituents selected from halo, alkyl, CN, NO₂, CO₂R, C(O)R, —O—R, —N(R')(R"), —N(R)C(O)R, —N(R)SO₂R, —SR, —C(O)N(R')(R"), —OC(O)R, —OC(O)N(R')(R"), SO₂, —SOR, —SO₃R, —SO₂N(R')(R"), phosphate, phosphonate, substituted and unsubstituted alkyl, substituted and unsubstituted alkenyl, substituted and unsubstituted cycloalkyl, substituted and unsubstituted cycloalkenyl, substituted and unsubstituted aryl and a substituted and unsubstituted heterocyclic group, wherein the substituted alkyl, substituted alkenyl, substituted cycloalkyl, substituted cycloalkenyl, substituted aryl and substituted heterocyclic group may be substituted with one or more of halo, CN, CF₃, CO₂R, C(O)R, C(O)NR₂, NR₂, NO₂, and OR.

The terms "aryl", "aromatic group", or "aromatic ring" as used herein contemplates substituted or unsubstituted single-ring aromatic groups (for example, phenyl, pyridyl, pyrazole, etc.) and polycyclic ring systems (naphthyl, quinoline, etc.). The polycyclic rings may have two or more rings in which two atoms are common to two adjoining rings (the rings are "fused") wherein at least one of the rings is aromatic, e.g., the other rings can be cycloalkyls, cycloalkenyls, aryl, heterocycles and/or heteroaryls. The aryl group may be optionally substituted with one or more substituents selected from halo, alkyl, CN, NO₂, CO₂R, C(O)R, —O—R, —N(R')(R"), —N(R)C(O)R, —N(R)SO₂R, —SR, —C(O)N(R')(R"), —OC(O)R, —OC(O)N(R')(R"), SO₂, —SOR, —SO₃R, —SO$_2$N(R')(R''), phosphate, phosphonate, substituted and unsubstituted alkyl, substituted and unsubstituted alkenyl, substituted and unsubstituted cycloalkyl, substituted and unsubstituted cycloalkenyl, substituted and unsubstituted aryl and a substituted and unsubstituted heterocyclic group, wherein the substituted alkyl, substituted alkenyl, substituted cycloalkyl, substituted cycloalkenyl, substituted aryl and substituted heterocyclic group may be substituted with one or more of halo, CN, CF$_3$, CO$_2$R, C(O)R, C(O)NR$_2$, NR$_2$, NO$_2$, and OR.

With respect to the above definitions, each R is independently selected from H, substituted and unsubstituted alkyl, substituted and unsubstituted cycloalkyl, substituted and unsubstituted cycloalkenyl, substituted and unsubstituted alkenyl, substituted and unsubstituted alkynyl, substituted and unsubstituted aralkyl, substituted and unsubstituted aryl and a substituted and unsubstituted heterocyclic group. Each R' and R'' are independently selected from H, substituted and unsubstituted alkyl, substituted and unsubstituted cycloalkyl, substituted and unsubstituted cycloalkenyl, substituted and unsubstituted alkenyl, substituted and unsubstituted alkynyl, substituted and unsubstituted aralkyl, substituted and unsubstituted aryl and substituted and unsubstituted heterocyclic group; or R' and R'' may be taken together with the nitrogen to which they are attached to form a 5- to 7-membered ring which may optionally contain a further heteroatom. The substituted alkyl, substituted cycloalkyl, substituted cycloalkenyl, substituted alkenyl, substituted alkynyl, substituted aralkyl, substituted aryl and substituted heterocyclic group may be substituted with one or more of halo, CN, CF$_3$, OH, CO$_2$H, NO$_2$, C$_{1-6}$alkyl, —O—(C$_{1-6}$alkyl), —NH$_2$, —NH(C$_{1-6}$alkyl) and —N(C$_{1-6}$alkyl)$_2$.

The term "heteroatom", particularly as a ring heteroatom, refers to N, O, and S.

All value ranges, for example those given for n and m, are inclusive over the entire range. Thus, a range of 0 to 4 would include the values 0, 1, 2, 3 and 4.

The present invention provides compounds of the formula I

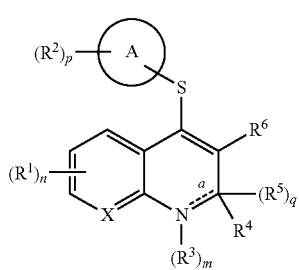

(I)

wherein:
a represents an optional double bond;
X is selected from N, C—H and C—R$^1$;
each R$^1$ is independently selected from alkyl, alkenyl, alkynyl, aralkyl, —(CH$_2$)$_r$—O—R$^{11}$, —(CH$_2$)$_r$—N(R$^{12}$)(R$^{13}$), —(CH$_2$)$_r$—N(R$^{11}$)—(CH$_2$)$_r$—C(O)R$^{14}$, —(CH$_2$)$_r$—N(R$^{11}$)SO$_2$R$^{11}$, —(CH$_2$)$_r$—SR$^{11}$, —(CH$_2$)$_r$—C(O)R$^{14}$, —(CH$_2$)$_r$—C(O)—(CH$_2$)$_s$OR$^{11}$, —(CH$_2$)$_r$—C(O)—(CH$_2$)$_s$N(R$^{12}$)(R$^{13}$), —(CH$_2$)$_r$O—(CH$_2$)$_s$—C(O)R$^{14}$, —(CH$_2$)$_r$OC(O)—(CH$_2$)$_s$N(R$^{12}$)(R$^{13}$), CN, CF$_3$, NO$_2$, SO$_2$, —SOR$^{11}$, —SO$_3$R$^{11}$, —SO$_2$N(R$^{12}$)(R$^{13}$), cycloalkyl, cycloalkenyl, halo, phosphate, phosphonate, aryl and a heterocyclic group;

additionally or alternatively two R$^1$ substituents on adjacent ring atoms may be combined to form a fused 5 or 6-membered ring, wherein the fused 5- or 6-membered ring may contain from 0 to 3 ring heteroatoms and may be further substituted with one or more substituents selected from R$^{11}$;

each R$^{11}$ is independently selected from H, alkyl, alkyl-O-alkyl, alkyl-O-aryl, alkenyl, alkynyl, cycloalkyl, cycloalkenyl, aralkyl, aryl and a heterocyclic group;

each R$^{12}$ and R$^{13}$ are independently selected from H, alkyl, cycloalkyl, cycloalkenyl, alkyl-O-alkyl, alkyl-O-aryl, alkenyl, alkynyl, aralkyl, aryl and a heterocyclic group; or R$^{12}$ and R$^{13}$ may be taken together with the nitrogen to which they are attached form a 5- to 7-membered ring which may optionally contain a further heteroatom and may be optionally substituted with up to three substituents selected from halo, CN, NO$_2$, alkyl, cycloalkyl, alkenyl, alkynyl, aralkyl, aryl, and a heterocyclic group;

each R$^{14}$ is independently selected from H, alkyl, —OH, —O-alkyl, —O-aryl, —O-aralkyl, -alkyl-O-alkyl, -alkyl-O-aryl, alkenyl, alkynyl, cycloalkyl, cycloalkenyl, aralkyl, aryl and a heterocyclic group;

r is 0 to 6;
s is 0 to 6;
n is 0 to 3;
A is a 5-, or 6-membered ring optionally comprising 0 to 3 heteroatoms;
each R$^2$ is selected from the group consisting of alkyl, alkenyl, alkynyl, aralkyl, —(CH$_2$)$_v$—O—R$^{21}$, —(CH$_2$)$_v$—N(R$^{22}$)(R$^{23}$), —(CH$_2$)$_v$—N(R$^{21}$)—(CH$_2$)$_w$—C(O)R$^{24}$, —(CH$_2$)$_v$—N(R$^{21}$)SO$_2$R$^{21}$, —(CH$_2$)$_v$—SR$^{21}$, —(CH$_2$)$_v$—C(O)R$^{24}$, —(CH$_2$)$_v$—C(O)—(CH$_2$)$_w$OR$^{21}$, —(CH$_2$)$_v$—C(O)(CH$_2$)$_w$—N(R$^{22}$)(R$^{23}$), —(CH$_2$)$_v$—O—(CH$_2$)$_w$—C(O)R$^{24}$, —(CH$_2$)$_v$—OC(O)—(CH$_2$)$_w$—N(R$^{22}$)(R$^{23}$), CN, CF$_3$, NO$_2$, SO$_2$, —SOR$^{21}$, —SO$_3$R$^{21}$, —SO$_2$N(R$^{22}$)(R$^{23}$), —NH—C(S)—NH—R$^{21}$, cycloalkyl, cycloalkenyl, halo, phosphate, phosphonate, aryl and a heterocyclic group;

additionally or alternatively two R$^2$ substituents on adjacent ring atoms may be combined to form a fused 5 or 6-membered ring, wherein the fused 5- or 6-membered ring may contain from 0 to 3 ring heteroatoms and may be further substituted with one or more substituents selected from R$^{21}$;

each R$^{21}$ is independently selected from H, alkyl, alkyl-O-alkyl, alkyl-O-aryl, alkenyl, alkynyl, cycloalkyl, cycloalkenyl, aralkyl, aryl and a heterocyclic group;

each R$^{22}$ and R$^{23}$ are independently selected from H, alkyl, cycloalkyl, cycloalkenyl, alkyl-O-alkyl, alkyl-O-aryl, alkenyl, alkynyl, aralkyl, aryl and a heterocyclic group; or R$^{22}$ and R$^{23}$ may be taken together with the nitrogen to which they are attached form a 5- to 7-membered ring which may optionally contain a further heteroatom and may be optionally substituted with up to three substituents selected from halo, CN, NO$_2$, alkyl, cycloalkyl, alkenyl, alkynyl, aralkyl, aryl, and a heterocyclic group, each R$^{24}$ is independently selected from H, alkyl, —OH, —O-alkyl, —O-aryl, —O-aralkyl, -alkyl-O-alkyl, -alkyl-O-aryl, alkenyl, alkynyl, cycloalkyl, cycloalkenyl, aralkyl, aryl and a heterocyclic group;

v is 0 to 6;
w is 0 to 6;
p is 0 to 3

$R^3$ is selected from the group consisting of H, alkyl, cycloalkyl, alkenyl, alkynyl, aralkyl, aryl, a heterocyclic group, —$(CH_2)_xC(O)R^{31}$, —$(CH_2)_xC(O)N(R^{32})(R^{33})$, $(CH_2)_xC(O)OR^{31}$, $R^{31}$ is selected from H, alkyl, cycloalkyl, cycloalkenyl, alkenyl, alkynyl, aralkyl, aryl and a heterocyclic group;

$R^{32}$ and $R^{33}$ are independently selected from H, alkyl, cycloalkyl, cycloalkenyl, alkenyl, alkynyl, aralkyl, aryl and a heterocyclic group;

or $R^{32}$ and $R^{33}$ may be taken together with the nitrogen to which they are attached to form a 5- to 7-membered ring which may optionally contain a further heteroatom and may be optionally substituted with up to three substituents selected from halo, CN, $NO_2$, alkyl, cycloalkyl, alkenyl, alkynyl, aralkyl, aryl, and a heterocyclic group;

x is 0 to 6;

m is 0 or 1;

$R^4$ is selected from the group consisting of H, halo, alkyl, cycloalkyl, alkenyl, alkynyl, aralkyl, aryl, a heterocyclic group, —$(CH_2)_y$—O—$R^{41}$, —$(CH_2)_y$—$N(R^{42})(R^{43})$, —$(CH_2)_y$—$N(R^{41})$—$(CH_2)_z$—$C(O)R^{41}$, —$(CH_2)_y$—$N(R^{41})SO_2R^{41}$, —$(CH_2)_y$—$SR^{41}$, —$(CH_2)_y$—$C(O)R^{41}$, —$(CH_2)_y$—$C(O)OR^{41}$, —$(CH_2)_y$—$C(O)(CH_2)_z$—$N(R^{42})(R^{43})$, —$(CH_2)_y$—$OC(O)R^{41}$, and —$(CH_2)_y$—$OC(O)$—$(CH_2)_z$—$N(R^{42})(R^{43})$;

each $R^{41}$ is independently selected from H, alkyl, cycloalkyl, cycloalkenyl, alkenyl, alkynyl, aralkyl, aryl and a heterocyclic group;

$R^{42}$ and $R^{43}$ are independently selected from H, alkyl, cycloalkyl, cycloalkenyl, alkenyl, alkynyl, aralkyl, aryl and a heterocyclic group;

or $R^{42}$ and $R^{43}$ may be taken together with the nitrogen to which they are attached to form a 5- to 7-membered ring which may optionally contain a further heteroatom and may be optionally substituted with up to three substituents selected from halo, CN, $NO_2$, alkyl, cycloalkyl, alkenyl, alkynyl, aralkyl, aryl, and a heterocyclic group;

y is 0 to 6;

z is 0 to 6;

$R^5$ is H;

or $R^4$ and $R^5$ taken together are =O;

q is 0 or 1; and $R^6$ is selected from H, halo, alkyl, cycloalkyl, alkenyl, alkynyl, aralkyl, aryl, and a heterocyclic group;

or a pharmaceutically acceptable salt or hydrate thereof.

In preferred embodiments of the invention, ring A is selected from an aryl group. In particularly preferred embodiments, ring A is phenyl.

In other preferred embodiments of the invention, $R^4$ and $R^5$ are taken together to form =O.

In other preferred embodiments of the invention, $R^6$ is H.

In one embodiment of the invention, $R^4$ and $R^5$ are taken together to form =O, $R^6$ is H and m is 1 to give a compound of the formula II:

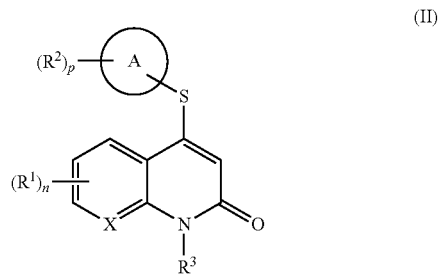

wherein:

X is selected from N, C—H and C—$R^1$;

each $R^1$ is independently selected from alkyl, alkenyl, alkynyl, aralkyl, —$(CH_2)_r$—O—$R^{11}$, —$(CH_2)_r$—$N(R^{12})(R^{13})$, —$(CH_2)_r$—$N(R^{11})$—$(CH_2)_s C(O)R^{14}$, $(CH_2)_r N$—$(R^{11})SO_2R^{11}$, —$(CH_2)_r$—$SR^{11}$, —$(CH_2)_r$—$C(O)R^{14}$, —$(CH_2)_r$—$C(O)$—$(CH_2)_s OR^{11}$, —$(CH_2)_r OC(O)$—$(CH_2)_s N(R^{12})(R^{13})$, —$(CH_2)_r O$—$(CH_2)$, —$C(O)R^{14}$, —$(CH_2)_r OC(O)$—$(CH_2)_s N(R^{12})(R^{13})$, CN, $CF_3$, $NO_2$, $SO_2$, —$SOR^{11}$, —$SO_3R^{11}$, —$SO_2N(R^{12})(R^{13})$, cycloalkyl, cycloalkenyl, halo, phosphate, phosphonate, aryl and a heterocyclic group;

additionally or alternatively two $R^1$ substituents on adjacent ring atoms may be combined to form a fused 5 or 6-membered ring, wherein the fused 5- or 6-membered ring may contain from 0 to 3 ring heteroatoms and may be further substituted with one or more substituents selected from $R^{11}$;

each $R^{11}$ is independently selected from H, alkyl, alkyl-O-alkyl, alkyl-O-aryl, alkenyl, alkynyl, cycloalkyl, cycloalkenyl, aralkyl, aryl and a heterocyclic group;

each $R^{12}$ and $R^{13}$ are independently selected from H, alkyl, cycloalkyl, cycloalkenyl, alkyl-O-alkyl, alkyl-O-aryl, alkenyl, alkynyl, aralkyl, aryl and a heterocyclic group; or $R^{12}$ and $R^{13}$ may be taken together with the nitrogen to which they are attached form a 5- to 7-membered ring which may optionally contain a further heteroatom and may be optionally substituted with up to three substituents selected from halo, CN, $NO_2$, alkyl, cycloalkyl, alkenyl, alkynyl, aralkyl, aryl, and a heterocyclic group;

each $R^{14}$ is independently selected from H, alkyl, —OH, —O-alkyl, —O-aryl, —O-aralkyl, -alkyl-O-alkyl, -alkyl-O-aryl, alkenyl, alkynyl, cycloalkyl, cycloalkenyl, aralkyl, aryl and a heterocyclic group;

r is 0 to 6;

s is 0 to 6;

n is 0 to 3;

A is a 5-, or 6-membered ring optionally comprising 0 to 3 heteroatoms;

each $R^2$ is selected from the group consisting of alkyl, alkenyl, alkynyl, aralkyl, —$(CH_2)_v$—O—$R^{21}$, —$(CH_2)_v$—$N(R^{22})(R^{23})$, —$(CH_2)_v$—$N(R^{21})$—$(CH_2)_w$—$C(O)R^{24}$, —$(CH_2)_v$—$N(R^{21})SO_2R^{21}$, —$(CH_2)$, —$SR^{21}$, —$(CH_2)_v$—$C(O)R^{24}$, —$(CH_2)_v$—$C(O)$—$(CH_2)_w OR^{21}$, —$(CH_2)_v$—$C(O)(CH_2)_w$—$N(R^{22})(R^{23})$, —$(CH_2)_v$—O—$(CH_2)_w$—$C(O)R^{24}$, —$(CH_2)_v$—$OC(O)$—$(CH_2)_w$—$N(R^{22})(R^{23})$, CN, $CF_3$, $NO_2$, $SO_2$, —$SOR^{21}$, —$SO_3R^{21}$, —$SO_2N(R^{22})(R^{23})$, —NH—C(S)—NH—$R^{21}$, cycloalkyl, cycloalkenyl, halo, phosphate, phosphonate, aryl and a heterocyclic group;

additionally or alternatively two $R^2$ substituents on adjacent ring atoms may be combined to form a fused 5 or 6-membered ring, wherein the fused 5- or 6-membered ring may contain from 0 to 3 ring heteroatoms and may be further substituted with one or more substituents selected from $R^{21}$;

each $R^{21}$ is independently selected from H, alkyl, alkyl-O-alkyl, alkyl-O-aryl, alkenyl, alkynyl, cycloalkyl, cycloalkenyl, aralkyl, aryl and a heterocyclic group;

each $R^{22}$ and $R^{23}$ are independently selected from H, alkyl, cycloalkyl, cycloalkenyl, alkyl-O-alkyl, alkyl-O-aryl, alkenyl, alkynyl, aralkyl, aryl and a heterocyclic group; or $R^{22}$ and $R^{23}$ may be taken together with the nitrogen to which they are attached form a 5- to 7-membered ring which may optionally contain a further heteroatom and may be optionally substituted with up to three substituents selected from halo, CN, $NO_2$, alkyl, cycloalkyl, alkenyl, alkynyl, aralkyl, aryl, and a heterocyclic group, each $R^{24}$ is independently selected from H, alkyl, —OH, —O-alkyl, —O-aryl, —O-aralkyl, -alkyl-O-alkyl, -alkyl-O-aryl, alkenyl, alkynyl, cycloalkyl, cycloalkenyl, aralkyl, aryl and a heterocyclic group;

v is 0 to 6;

w is 0 to 6;

p is 0 to 3

$R^3$ is selected from the group consisting of H, alkyl, cycloalkyl, alkenyl, alkynyl, aralkyl, aryl, a heterocyclic group, —$(CH_2)_xC(O)R^{31}$, —$(CH_2)_xC(O)N(R^{32})(R^{33})$, $(CH_2)_xC(O)OR^{31}$, $R^{31}$ is selected from H, alkyl, cycloalkyl, cycloalkenyl, alkenyl, alkynyl, aralkyl, aryl and a heterocyclic group;

$R^{32}$ and $R^{33}$ are independently selected from H, alkyl, cycloalkyl, cycloalkenyl, alkenyl, alkynyl, aralkyl, aryl and a heterocyclic group;

or $R^{32}$ and $R^{33}$ may be taken together with the nitrogen to which they are attached to form a 5- to 7-membered ring which may optionally contain a further heteroatom and may be optionally substituted with up to three substituents selected from halo, CN, $NO_2$, alkyl, cycloalkyl, alkenyl, alkynyl, aralkyl, aryl, and a heterocyclic group; and x is 0 to 6;

or a pharmaceutically acceptable salt or hydrate thereof.

In a further embodiment of the invention, $R^4$ and $R^5$ are taken together to form =O, $R^6$ is H, m is 1, and ring A is phenyl to give a compound of the formula III:

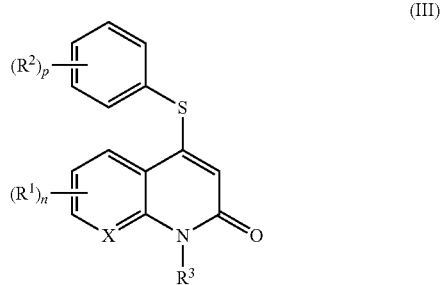

(III)

wherein:

X is selected from N, C—H and C—$R^1$;

each $R^1$ is independently selected from alkyl, alkenyl, alkynyl, aralkyl, —$(CH_2)_r$—O—$R^{11}$, —$(CH_2)_r$—$N(R^{12})(R^{13})$, —$(CH_2)_r$—$N(R^{11})$—$(CH_2)_s$C(O)$R^{14}$, —$(CH_2)_r$—$N(R^{11})SO_2R^{11}$, —$(CH_2)_r$—$SR^{11}$, —$(CH_2)_r$—C(O)$R^{14}$, —$(CH_2)_r$—C(O)—$(CH_2)_sOR^{11}$, —$(CH_2)_r$—C(O)—$(CH_2)_sN(R^{12})(R^{13})$, —$(CH_2)_r$O—$(CH_2)$, —C(O)$R^{14}$, —$(CH_2)_rOC(O)$—$(CH_2)_sN(R^{12})(R^{13})$, CN, $CF_3$, $NO_2$, $SO_2$, —$SOR^{11}$, —$SO_3R^{11}$, —$SO_2N(R^{12})(R^{13})$, cycloalkyl, cycloalkenyl, halo, phosphate, phosphonate, aryl and a heterocyclic group;

additionally or alternatively two $R^{11}$ substituents on adjacent ring atoms may be combined to form a fused 5 or 6-membered ring, wherein the fused 5- or 6-membered ring may contain from 0 to 3 ring heteroatoms and may be further substituted with one or more substituents selected from $R^{11}$;

each $R^{11}$ is independently selected from H, alkyl, alkyl-O-alkyl, alkyl-O-aryl, alkenyl, alkynyl, cycloalkyl, cycloalkenyl, aralkyl, aryl and a heterocyclic group;

each $R^{12}$ and $R^{13}$ are independently selected from H, alkyl, cycloalkyl, cycloalkenyl, alkyl-O-alkyl, alkyl-O-aryl, alkenyl, alkynyl, aralkyl, aryl and a heterocyclic group; or $R^{12}$ and $R^{13}$ may be taken together with the nitrogen to which they are attached form a 5- to 7-membered ring which may optionally contain a further heteroatom and may be optionally substituted with up to three substituents selected from halo, CN, $NO_2$, alkyl, cycloalkyl, alkenyl, alkynyl, aralkyl, aryl, and a heterocyclic group;

each $R^{14}$ is independently selected from H, alkyl, —OH, —O-alkyl, —O-aryl, —O-aralkyl, -alkyl-O-alkyl, -alkyl-O-aryl, alkenyl, alkynyl, cycloalkyl, cycloalkenyl, aralkyl, aryl and a heterocyclic group;

r is 0 to 6;

s is 0 to 6;

n is 0 to 3;

each $R^2$ is selected from the group consisting of alkyl, alkenyl, alkynyl, aralkyl, —$(CH_2)_v$—O—$R^{21}$, —$(CH_2)_v$—$N(R^{22})(R^{23})$, —$(CH_2)_v$—$N(R^{21})$—$(CH_2)_w$—C(O)$R^{24}$, —$(CH_2)_v$—$N(R^{21})SO_2R^{21}$, —$(CH_2)_v$—$SR^{21}$, —$(CH_2)_v$—C(O)$R^{24}$, —$(CH_2)_v$—C(O)—$(CH_2)_w$OR, —$(CH_2)_v$—C(O)($CH_2)_w$—$N(R^{22})(R^{23})$, —$(CH_2)_v$—O—$(CH_2)_w$—C(O)$R^{24}$, —$(CH_2)_v$—OC(O)—$(CH_2)_w$—$N(R^{22})(R^{23})$, CN, $CF_3$, $NO_2$, $SO_2$, —$SOR^{21}$, —$SO_3R^{21}$, —$SO_2N(R^{22})(R^{23})$, —NH—C(S)—NH—$R^{21}$, cycloalkyl, cycloalkenyl, halo, phosphate, phosphonate, aryl and a heterocyclic group;

additionally or alternatively two $R^2$ substituents on adjacent ring atoms may be combined to form a fused 5 or 6-membered ring, wherein the fused 5- or 6-membered ring may contain from 0 to 3 ring heteroatoms and may be further substituted with one or more substituents selected from $R^{21}$;

each $R^{21}$ is independently selected from H, alkyl, alkyl-O-alkyl, alkyl-O-aryl, alkenyl, alkynyl, cycloalkyl, cycloalkenyl, aralkyl, aryl and a heterocyclic group;

each $R^{22}$ and $R^{23}$ are independently selected from H, alkyl, cycloalkyl, cycloalkenyl, alkyl-O-alkyl, alkyl-O-aryl, alkenyl, alkynyl, aralkyl, aryl and a heterocyclic group; or $R^{22}$ and $R^{23}$ may be taken together with the nitrogen to which they are attached form a 5- to 7-membered ring which may optionally contain a further heteroatom and may be optionally substituted with up to three substituents selected from halo, CN, $NO_2$, alkyl, cycloalkyl, alkenyl, alkynyl, aralkyl, aryl, and a heterocyclic group, each $R^{24}$ is independently selected from H, alkyl, —OH, —O-alkyl, —O-aryl, —O-aralkyl, -alkyl-O-alkyl, -alkyl-O-aryl, alkenyl, alkynyl, cycloalkyl, cycloalkenyl, aralkyl, aryl and a heterocyclic group;

v is 0 to 6;

w is 0 to 6;

p is 0 to 3

R³ is selected from the group consisting of H, alkyl, cycloalkyl, alkenyl, alkynyl, aralkyl, aryl, a heterocyclic group, —(CH₂)$_x$C(O)R³¹, —(CH₂)$_x$C(O)N(R³²)(R³³), (CH₂)$_x$C(O)OR³¹, R³¹ is selected from H, alkyl, cycloalkyl, cycloalkenyl, alkenyl, alkynyl, aralkyl, aryl and a heterocyclic group;

R³² and R³³ are independently selected from H, alkyl, cycloalkyl, cycloalkenyl, alkenyl, alkynyl, aralkyl, aryl and a heterocyclic group;

or R³² and R³³ may be taken together with the nitrogen to which they are attached to form a 5- to 7-membered ring which may optionally contain a further heteroatom and may be optionally substituted with up to three substituents selected from halo, CN, NO₂, alkyl, cycloalkyl, alkenyl, alkynyl, aralkyl, aryl, and a heterocyclic group; and x is 0 to 6;

or a pharmaceutically acceptable salt or hydrate thereof.

In further preferred embodiment, the invention provides a compound of the formula III$_a$:

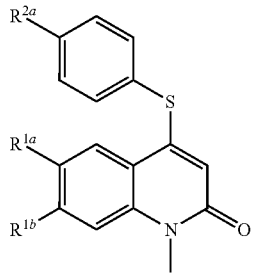

wherein:

R$^{1a}$ and R$^{1b}$ are independently selected from H, alkyl, alkenyl, alkynyl, aralkyl, —(CH₂)$_r$—O—R¹¹, —(CH₂)$_r$—N(R¹²)(R¹³), —(CH₂)$_r$—N(R¹¹)—(CH₂)$_s$C(O)R¹⁴, —(CH₂)$_r$—N(R¹¹)SO₂R¹¹, —(CH₂)$_r$—SR¹¹, —(CH₂)$_r$—C(O)R¹⁴, —(CH₂)$_r$—C(O)—(CH₂)$_s$OR¹¹, —(CH₂)$_r$—C(O)—(CH₂)$_s$N(R¹²)(R¹³), —(CH₂)$_r$O—(CH₂)$_s$—C(O)R¹⁴, —(CH₂)$_r$OC(O)—(CH₂)$_s$N(R¹²)(R¹³), CN, CF₃, NO₂, SO₂, —SOR¹¹, —SO₃R¹¹, —SO₂N(R¹²)(R¹³), cycloalkyl, cycloalkenyl, halo, phosphate, phosphonate, aryl and a heterocyclic group;

each R¹¹ is independently selected from H, alkyl, alkyl-O-alkyl, alkyl-O-aryl, alkenyl, alkynyl, cycloalkyl, cycloalkenyl, aralkyl, aryl and a heterocyclic group;

each R¹² and R¹³ are independently selected from H, alkyl, cycloalkyl, cycloalkenyl, alkyl-O-alkyl, alkyl-O-aryl, alkenyl, alkynyl, aralkyl, aryl and a heterocyclic group;

or R¹² and R¹³ may be taken together with the nitrogen to which they are attached form a 5- to 7-membered ring which may optionally contain a further heteroatom and may be optionally substituted with up to three substituents selected from halo, CN, NO₂, alkyl, cycloalkyl, alkenyl, alkynyl, aralkyl, aryl, and a heterocyclic group;

each R¹⁴ is independently selected from H, alkyl, —OH, —O-alkyl, —O-aryl, —O-aralkyl, -alkyl-O-alkyl, -alkyl-O-aryl, alkenyl, alkynyl, cycloalkyl, cycloalkenyl, aralkyl, aryl and a heterocyclic group;

r is 0 to 6;

s is 0 to 6;

R$^{2a}$ is selected from the group consisting of H, alkyl, alkenyl, alkynyl, aralkyl, —(CH₂)$_v$—O—R²¹, —(CH₂)$_v$—N(R²²)(R²³), —(CH₂)$_v$—N(R²¹)—(CH₂)$_w$—C(O)R²⁴, —(CH₂)$_v$—N(R²¹)SO₂R²¹, —(CH₂)$_v$—SR²¹, —(CH₂)$_v$—C(O)R²⁴, —(CH₂)$_v$—C(O)—(CH₂)$_w$OR²¹, —(CH₂)$_v$—C(O)(CH₂)$_w$—N(R²²)(R²³), —(CH₂)$_v$—O—(CH₂)$_w$—C(O)R²⁴, —(CH₂)$_v$—OC(O)—(CH₂)$_w$—N(R²²)(R²³), CN, CF₃, NO₂, SO₂, —SOR²¹, —SO₃R²¹, —SO₂N(R²²)(R²³), —NH—C(S)—NH—R²¹, cycloalkyl, cycloalkenyl, halo, phosphate, phosphonate, aryl and a heterocyclic group;

each R²¹ is independently selected from H, alkyl, alkyl-O-alkyl, alkyl-O-aryl, alkenyl, alkynyl, cycloalkyl, cycloalkenyl, aralkyl, aryl and a heterocyclic group;

each R²² and R²³ are independently selected from H, alkyl, cycloalkyl, cycloalkenyl, alkyl-O-alkyl, alkyl-O-aryl, alkenyl, alkynyl, aralkyl, aryl and a heterocyclic group;

or R²² and R²³ may be taken together with the nitrogen to which they are attached form a 5- to 7-membered ring which may optionally contain a further heteroatom and may be optionally substituted with up to three substituents selected from halo, CN, NO₂, alkyl, cycloalkyl, alkenyl, alkynyl, aralkyl, aryl, and a heterocyclic group, each R²⁴ is independently selected from H, alkyl, —OH, —O-alkyl, —O-aryl, —O-aralkyl, -alkyl-O-alkyl, -alkyl-O-aryl, alkenyl, alkynyl, cycloalkyl, cycloalkenyl, aralkyl, aryl and a heterocyclic group;

v is 0 to 6;

w is 0 to 6; and p is 0 to 3.

In further preferred embodiments of the invention for compounds having the formula III$_a$, R$^{1a}$ and R$^{2a}$ are independently selected from H, —NH₂, halo, alkyl, and —O-alkyl, and R$^{2a}$ is selected from H and halo.

In further preferred embodiment of the invention, R⁶ is H, and m is 0 to give a compound of the formula IV:

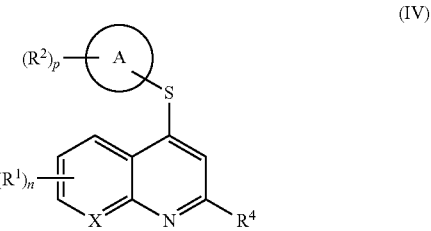

wherein:

X is selected from N, C—H and C—R¹;

each R¹ is independently selected from alkyl, alkenyl, alkynyl, aralkyl, —(CH₂)$_r$—O—R¹¹, —(CH₂)$_r$—N(R¹²)(R¹³), —(CH₂)$_r$—N(R¹¹)—(CH₂)$_r$—C(O)R¹⁴, (CH₂)$_r$—N(R¹¹)SO₂R¹¹, —(CH₂)$_r$—SR¹¹, —(CH₂)$_r$—C(O)R¹⁴, —(CH₂)$_r$—C(O)—(CH₂)$_s$OR¹¹, —(CH₂)$_r$—C(O)—(CH₂)$_s$N(R¹²)(R¹³), —(CH₂)$_r$O—(CH₂), —C(O)R¹⁴, —(CH₂)$_r$OC(O)—(CH₂)$_s$N(R¹²)(R¹³), CN, CF₃, NO₂, SO₂, —SOR¹¹, —SO₃R¹¹, —SO₂N(R¹²)(R¹³), cycloalkyl, cycloalkenyl, halo, phosphate, phosphonate, aryl and a heterocyclic group;

additionally or alternatively two R¹ substituents on adjacent ring atoms may be combined to form a fused 5 or 6-membered ring, wherein the fused 5- or 6-membered ring may contain from 0 to 3 ring heteroatoms and may be further substituted with one or more substituents selected from R¹¹;

each R¹¹ is independently selected from H, alkyl, alkyl-O-alkyl, alkyl-O-aryl, alkenyl, alkynyl, cycloalkyl, cycloalkenyl, aralkyl, aryl and a heterocyclic group;

each $R^{12}$ and $R^{13}$ are independently selected from H, alkyl, cycloalkyl, cycloalkenyl, alkyl-O-alkyl, alkyl-O-aryl, alkenyl, alkynyl, aralkyl, aryl and a heterocyclic group; or $R^{12}$ and $R^{13}$ may be taken together with the nitrogen to which they are attached form a 5- to 7-membered ring which may optionally contain a further heteroatom and may be optionally substituted with up to three substituents selected from halo, CN, $NO_2$, alkyl, cycloalkyl, alkenyl, alkynyl, aralkyl, aryl, and a heterocyclic group;

each $R^{14}$ is independently selected from H, alkyl, —OH, —O-alkyl, —O-aryl, —O-aralkyl, -alkyl-O-alkyl, -alkyl-O-aryl, alkenyl, alkynyl, cycloalkyl, cycloalkenyl, aralkyl, aryl and a heterocyclic group;

r is 0 to 6;
s is 0 to 6;
n is 0 to 3;
A is a 5-, or 6-membered ring optionally comprising 0 to 3 heteroatoms;

each $R^2$ is selected from the group consisting of alkyl, alkenyl, alkynyl, aralkyl, —$(CH_2)_v$—O—$R^{21}$, —$(CH_2)_v$—N$(R^{22})(R^{23})$, —$(CH_2)_v$—N$(R^2)$—$(CH_2)_w$—C(O)$R^{24}$, —$(CH_2)_v$—N$(R^{21})SO_2R^{21}$, —$(CH_2)_v$—S$R^{21}$, —$(CH_2)_v$—C(O)$R^{24}$, —$(CH_2)_v$—C(O)—$(CH_2)_wOR^{21}$, —$(CH_2)_v$—C(O)$(CH_2)_w$—N$(R^{22})(R^{23})$, —$(CH_2)_v$—O—$(CH_2)_w$—C(O)$R^{24}$, —$(CH_2)_v$—OC(O)—$(CH_2)_w$—N$(R^{22})(R^{23})$, CN, $CF_3$, $NO_2$, $SO_2$, —SO$R^{21}$, —$SO_3R^{21}$, —$SO_2N(R^{22})(R^{23})$, —NH—C(S)—NH—$R^{21}$, cycloalkyl, cycloalkenyl, halo, phosphate, phosphonate, aryl and a heterocyclic group;

additionally or alternatively two $R^2$ substituents on adjacent ring atoms may be combined to form a fused 5 or 6-membered ring, wherein the fused 5- or 6-membered ring may contain from 0 to 3 ring heteroatoms and may be further substituted with one or more substituents selected from $R^{21}$;

each $R^{21}$ is independently selected from H, alkyl, alkyl-O-alkyl, alkyl-O-aryl, alkenyl, alkynyl, cycloalkyl, cycloalkenyl, aralkyl, aryl and a heterocyclic group;

each $R^{22}$ and $R^{23}$ are independently selected from H, alkyl, cycloalkyl, cycloalkenyl, alkyl-O-alkyl, alkyl-O-aryl, alkenyl, alkynyl, aralkyl, aryl and a heterocyclic group; or $R^{22}$ and $R^{23}$ may be taken together with the nitrogen to which they are attached form a 5- to 7-membered ring which may optionally contain a further heteroatom and may be optionally substituted with up to three substituents selected from halo, CN, $NO_2$, alkyl, cycloalkyl, alkenyl, alkynyl, aralkyl, aryl, and a heterocyclic group, each $R^{24}$ is independently selected from H, alkyl, —OH, —O-alkyl, —O-aryl, —O-aralkyl, -alkyl-O-alkyl, -alkyl-O-aryl, alkenyl, alkynyl, cycloalkyl, cycloalkenyl, aralkyl, aryl and a heterocyclic group;

v is 0 to 6;
w is 0 to 6;
p is 0 to 3;

$R^4$ is selected from the group consisting of H, halo, alkyl, cycloalkyl, alkenyl, alkynyl, aralkyl, aryl, a heterocyclic group, —$(CH_2)_y$—O—$R^{41}$, —$(CH_2)_y$—N$(R^{42})(R^{43})$, —$(CH_2)_y$—N$(R^{41})$—$(CH_2)_z$—C(O)$R^{41}$, —$(CH_2)_y$—N$(R^{41})SO_2R^{41}$, —$(CH_2)_y$—S$R^{41}$, —$(CH_2)_y$—C(O)$R^{41}$, —$(CH_2)_y$—C(O)O$R^{41}$, —$(CH_2)_y$—C(O)$(CH_2)_z$—N$(R^{42})(R^{43})$, —$(CH_2)_y$—OC(O)$R^{41}$, and —$(CH_2)_y$—OC(O)—$(CH_2)_z$—N$(R^{42})(R^{43})$;

each $R^{41}$ is independently selected from H, alkyl, cycloalkyl, cycloalkenyl, alkenyl, alkynyl, aralkyl, aryl and a heterocyclic group;

$R^{42}$ and $R^{43}$ are independently selected from H, alkyl, cycloalkyl, cycloalkenyl, alkenyl, alkynyl, aralkyl, aryl and a heterocyclic group;

or $R^{42}$ and $R^{43}$ may be taken together with the nitrogen to which they are attached to form a 5- to 7-membered ring which may optionally contain a further heteroatom and may be optionally substituted with up to three substituents selected from halo, CN, $NO_2$, alkyl, cycloalkyl, alkenyl, alkynyl, aralkyl, aryl, and a heterocyclic group;

y is 0 to 6; and
z is 0 to 6;

or a pharmaceutically acceptable salt or hydrate thereof.

In a preferred embodiment for compounds of the formula IV, $R^7$ is selected to be an aryl group.

In another embodiment of the invention, $R^6$ is H, m is 0, and ring A is phenyl to give a compound of the formula V:

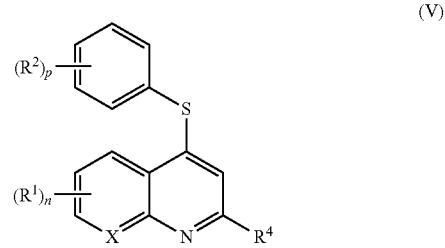

(V)

wherein:
X is selected from N, C—H and C—$R^1$;

each $R^1$ is independently selected from alkyl, alkenyl, alkynyl, aralkyl, —$(CH_2)_r$—O—$R^{11}$, —$(CH_2)_r$—N$(R^{12})(R^{13})$, —$(CH_2)_r$—N$(R^{11})$—$(CH_2)_sC(O)R^{14}$, —$(CH_2)_r$—N$(R^{11})SO_2R^{11}$, —$(CH_2)_r$—S$R^{11}$, —$(CH_2)_r$—C(O)$R^{14}$, —$(CH_2)_r$—C(O)—$(CH_2)_sOR^{11}$, —$(CH_2)_r$—C(O)—$(CH_2)_sN(R^{12})(R^{13})$, —$(CH_2)_r$O—$(CH_2)_s$—C(O)$R^{14}$, —$(CH_2)_r$OC(O)—$(CH_2)_sN(R^{12})(R^{13})$, CN, $CF_3$, $NO_2$, $SO_2$, —SO$R^{11}$, —$SO_3R^{11}$, —$SO_2N(R^{12})(R^{13})$, cycloalkyl, cycloalkenyl, halo, phosphate, phosphonate, aryl and a heterocyclic group;

additionally or alternatively two $R^1$ substituents on adjacent ring atoms may be combined to form a fused 5 or 6-membered ring, wherein the fused 5- or 6-membered ring may contain from 0 to 3 ring heteroatoms and may be further substituted with one or more substituents selected from $R^{11}$;

each $R^{11}$ is independently selected from H, alkyl, alkyl-O-alkyl, alkyl-O-aryl, alkenyl, alkynyl, cycloalkyl, cycloalkenyl, aralkyl, aryl and a heterocyclic group;

each $R^{12}$ and $R^{13}$ are independently selected from H, alkyl, cycloalkyl, cycloalkenyl, alkyl-O-alkyl, alkyl-O-aryl, alkenyl, alkynyl, aralkyl, aryl and a heterocyclic group; or $R^{12}$ and $R^{13}$ may be taken together with the nitrogen to which they are attached form a 5- to 7-membered ring which may optionally contain a further heteroatom and may be optionally substituted with up to three substituents selected from halo, CN, $NO_2$, alkyl, cycloalkyl, alkenyl, alkynyl, aralkyl, aryl, and a heterocyclic group;

each $R^{14}$ is independently selected from H, alkyl, —OH, —O-alkyl, —O-aryl, —O-aralkyl, -alkyl-O-alkyl, -alkyl-O-aryl, alkenyl, alkynyl, cycloalkyl, cycloalkenyl, aralkyl, aryl and a heterocyclic group;

r is 0 to 6;
s is 0 to 6;
n is 0 to 3;

each $R^2$ is selected from the group consisting of alkyl, alkenyl, alkynyl, aralkyl, —$(CH_2)_v$—O—$R^{21}$, —$(CH_2)_v$—N$(R^{22})(R^{23})$, —$(CH_2)_v$—N$(R^{21})$—$(CH_2)_w$—C(O)$R^{24}$, —$(CH_2)_v$—N$(R^{21})SO_2R^{21}$, —$(CH_2)_v$—S$R^{21}$, —$(CH_2)_v$—C(O)$R^{24}$, —$(CH_2)_v$—C(O)—$(CH_2)_w$O$R^{21}$, —$(CH_2)_v$—C(O)$(CH_2)_w$—N$(R^{22})(R^{23})$, —$(CH_2)_v$—O—$(CH_2)_w$—C(O)$R^{24}$, —$(CH_2)_v$—OC(O)—$(CH_2)_w$—N$(R^{22})(R^{23})$, CN, $CF_3$, $NO_2$, $SO_2$, —SO$R^{21}$, —$SO_3R^{21}$, —$SO_2N(R^{22})(R^{23})$, —NH—C(S)—NH—$R^{21}$, cycloalkyl, cycloalkenyl, halo, phosphate, phosphonate, aryl and a heterocyclic group;

additionally or alternatively two $R^2$ substituents on adjacent ring atoms may be combined to form a fused 5 or 6-membered ring, wherein the fused 5- or 6-membered ring may contain from 0 to 3 ring heteroatoms and may be further substituted with one or more substituents selected from $R^{21}$;

each $R^{21}$ is independently selected from H, alkyl, alkyl-O-alkyl, alkyl-O-aryl, alkenyl, alkynyl, cycloalkyl, cycloalkenyl, aralkyl, aryl and a heterocyclic group;

each $R^{22}$ and $R^{23}$ are independently selected from H, alkyl, cycloalkyl, cycloalkenyl, alkyl-O-alkyl, alkyl-O-aryl, alkenyl, alkynyl, aralkyl, aryl and a heterocyclic group; or $R^{22}$ and $R^{23}$ may be taken together with the nitrogen to which they are attached form a 5- to 7-membered ring which may optionally contain a further heteroatom and may be optionally substituted with up to three substituents selected from halo, CN, $NO_2$, alkyl, cycloalkyl, alkenyl, alkynyl, aralkyl, aryl, and a heterocyclic group, each $R^{24}$ is independently selected from H, alkyl, —OH, —O-alkyl, —O-aryl, —O-aralkyl, -alkyl-O-alkyl, -alkyl-O-aryl, alkenyl, alkynyl, cycloalkyl, cycloalkenyl, aralkyl, aryl and a heterocyclic group;

v is 0 to 6;
w is 0 to 6;
p is 0 to 3;

$R^4$ is selected from the group consisting of H, halo, alkyl, cycloalkyl, alkenyl, alkynyl, aralkyl, aryl, a heterocyclic group, —$(CH_2)_y$—O—$R^{41}$, —$(CH_2)_y$—N$(R^{42})(R^{43})$, —$(CH_2)_y$—N$(R^{41})$—$(CH_2)_z$—C(O)$R^{41}$, —$(CH_2)_y$—N$(R^{41})SO_2R^{41}$, —$(CH_2)_y$—S$R^{41}$, —$(CH_2)_y$—C(O)$R^{41}$, —$(CH_2)_y$—C(O)O$R^{41}$, —$(CH_2)_y$—C(O)($CH_2$), —N$(R^{42})(R^{43})$, —$(CH_2)_y$—OC(O)$R^{41}$, and —$(CH_2)_y$—OC(O)—$(CH_2)$, —N$(R^{42})(R^{43})$;

each $R^{41}$ is independently selected from H, alkyl, cycloalkyl, cycloalkenyl, alkenyl, alkynyl, aralkyl, aryl and a heterocyclic group;

$R^{42}$ and $R^{43}$ are independently selected from H, alkyl, cycloalkyl, cycloalkenyl, alkenyl, alkynyl, aralkyl, aryl and a heterocyclic group; or $R^{42}$ and $R^{43}$ may be taken together with the nitrogen to which they are attached to form a 5- to 7-membered ring which may optionally contain a further heteroatom and may be optionally substituted with up to three substituents selected from halo, CN, $NO_2$, alkyl, cycloalkyl, alkenyl, alkynyl, aralkyl, aryl, and a heterocyclic group;

y is 0 to 6; and
z is 0 to 6;

or a pharmaceutically acceptable salt or hydrate thereof.

The substances according to the invention may also be present as salts. In the context of the invention, preference is given to pharmaceutically acceptable salts. "Pharmaceutically acceptable salts" refers to an acid addition salt or a basic addition salt of a compound of the invention in which the resulting counter ion is understood in the art to be generally acceptable for pharmaceutical uses. Pharmaceutically acceptable salts can be salts of the compounds according to the invention with inorganic or organic acids. Preference is given to salts with inorganic acids, such as, for example, hydrochloric acid, hydrobromic acid, phosphoric acid or sulfuric acid, or to salts with organic carboxylic or sulfonic acids, such as, for example, acetic acid, maleic acid, fumaric acid, malic acid, citric acid, tartaric acid, lactic acid, benzoic acid, or methanesulfonic acid, ethanesulfonic acid, phenylsulfonic acid, toluenesulfonic acid or naphthalenedisulfonic acid. Pharmaceutically acceptable salts can also be metal or ammonium salts of the compounds according to the invention. Particular preference is given to, for example, sodium, potassium, magnesium or calcium salts, and also to ammonium salts which are derived from ammonia or organic amines, such as, for example, ethylamine, di- or triethylamine, di- or triethanolamine, dicyclohexylamine, dimethylaminoethanol, arginine, lysine, ethylenediamine or 2-phenylethylamine. (see, Berge et al. *J. Pharm. Sci.* 1977, 66, 1-19.)

When one or more chiral centers are present in the compounds of the present invention, the individual isomers and mixtures thereof (e.g., racemates, etc.) are intended to be encompassed by the formulae depicted herein. In certain embodiments, compounds of the invention may exist in several tautomeric forms. Accordingly, the chemical structures depicted herein encompass all possible tautomeric forms of the illustrated compounds. Compounds of the invention may exist in various hydrated forms.

It is understood that when n is a value greater than 1, each $R^1$ group may be selected independently. Thus, when more than one $R^1$ group is present, the $R^1$ groups may be selected from any of the stated groups so as to be the same or different. This also holds true for any other group or substituent which may be selected independently from among various groups or values.

In another aspect of the invention, a synthetic process for the preparation of compounds of the invention is provided. The inventive process uses mild reaction conditions, which provides a high substituent tolerance. The product is obtained in high yield and high purity. A process of the present invention is illustrated by Scheme I:

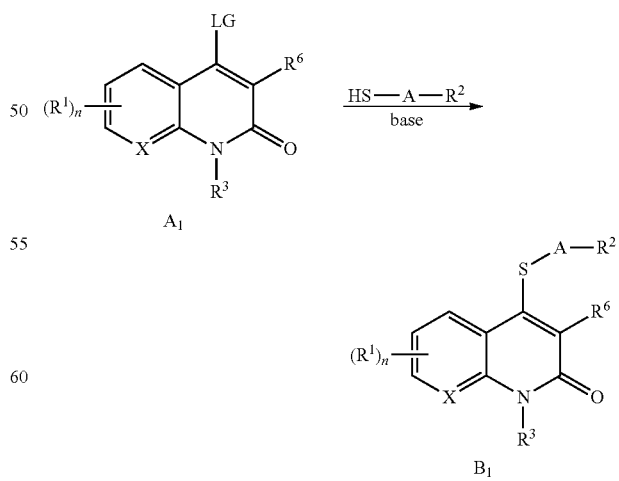

$A_1$ may be treated with a thiol (HS-A-$R^2$) in the presence of an appropriate base. LG represents a leaving group, such as halo, aryl sulfones (tosyl, etc.), triflate or other appropriate leaving group as would be recognized by the ordinarily skilled practitioner. A preferred leaving group is halo, particularly Cl. The base may be selected from amine bases, hydroxide salts (non-limiting examples include sodium hydroxide and tetraalkylamonium hydroxides), carbonate salts, hydrides, alkoxide salts (non-limiting examples include sodium methoxide and potassium t-butoxide) and the like. Hydrides, such as sodium hydride, are preferred bases.

In other embodiments, compounds of the invention may be prepared according the reactions provided in Scheme 2:

Scheme 2

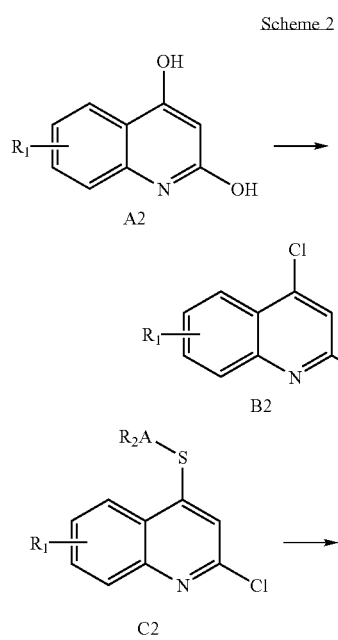

An optionally substituted 2,4-quinolinediol A2 can be converted to the corresponding 2,4-dichloroquinoline B2, for example by treatment with POCl$_3$, either neat or in a solvent. The solvent may be a polar aprotic solvent. The 2,4-dichloroquinoline B2 may be treated with a thiol (HS-A-R$^2$) in the presence of an appropriate base. The base may be selected from amine bases, hydroxide salts (non-limiting examples include sodium hydroxide and tetraalkylamonium hydroxides), carbonate salts, hydrides, alkoxide salts (non-limiting examples include sodium methoxide and potassium t-butoxide) and the like. The 2-chloro-4-thioquinoline C2 may be converted to D2, for example by treatment with HCl in TFA.

In other embodiments, compounds of the invention may be prepared according the reactions provided in Scheme 3:

Scheme 3

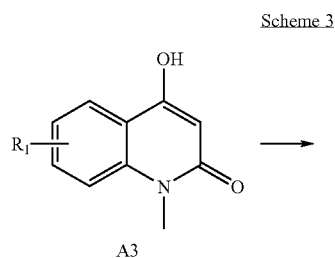

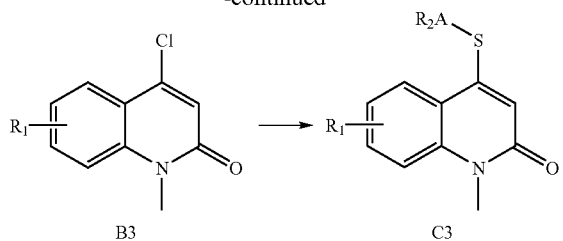

An optionally substituted 4-hydroxy-2-quinolone A3 can be converted to the corresponding 4-chloro-2-quinolone B3, for example by treatment with POCl$_3$, either neat or in a solvent. The solvent may be a polar aprotic solvent. The 4-chloro-2-quinolone B3 may be treated with a thiol (HS-A-R$^2$) in the presence of an appropriate base. The base may be selected from amine bases, hydroxide salts (non-limiting examples include sodium hydroxide and tetraalkylamonium hydroxides), carbonate salts, hydrides, alkoxide salts (non-limiting examples include sodium methoxide and potassium t-butoxide) and the like.

In other embodiments, compounds of the invention may be prepared according the reactions provided in Scheme 4:

Scheme 4

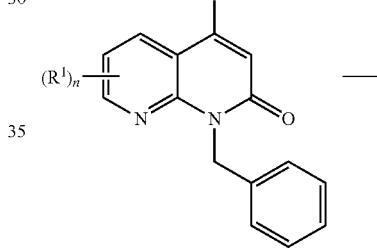

An optionally substituted 1-benzyl-4-hydroxy-naphthyridin-2-one A4 may be treated with POCl$_3$, either neat or in a solvent to give the corresponding 1-benzyl-4-chloro-naphthyridin-2-one B4 and the corresponding 2,4-dichloronaphthyridine. The solvent may be a polar aprotic solvent.

In other embodiments, compounds of the invention may be prepared according the reactions provided in Scheme 5:

Scheme 5

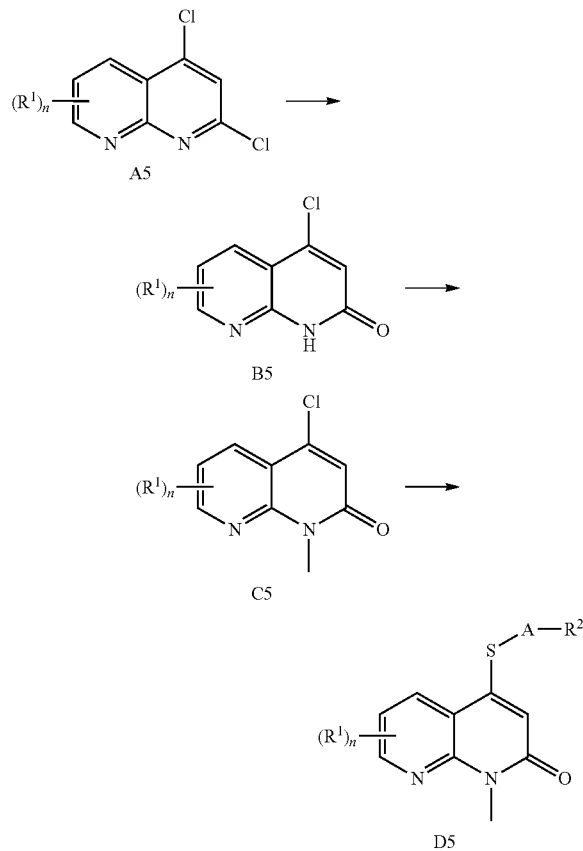

The 2,4-dichloronaphthyridine A5 may be converted to B5, for example by treatment with HCl in a polar aprotic solvent with heating, typically under reflux. B5 is treated with an appropriate base and methyl iodide in a polar aprotic solvent to give C5. The base may be selected from hydroxide salts (non-limiting examples include sodium hydroxide and tetraalkylamonium hydroxides), carbonate salts, hydrides, alkoxide salts (non-limiting examples include sodium methoxide and potassium t-butoxide) and the like. C5 may be treated with a thiol (HS-A-$R^2$) in the presence of an appropriate base. The base may be selected from amine bases, hydroxide salts (non-limiting examples include sodium hydroxide and tetraalkylamonium hydroxides), carbonate salts, hydrides, alkoxide salts (non-limiting examples include sodium methoxide and potassium t-butoxide) and the like.

Scheme 6

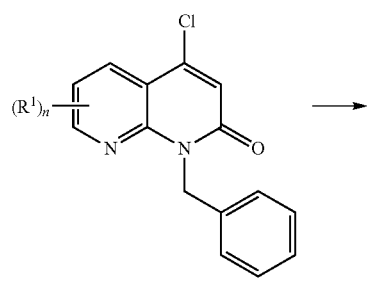

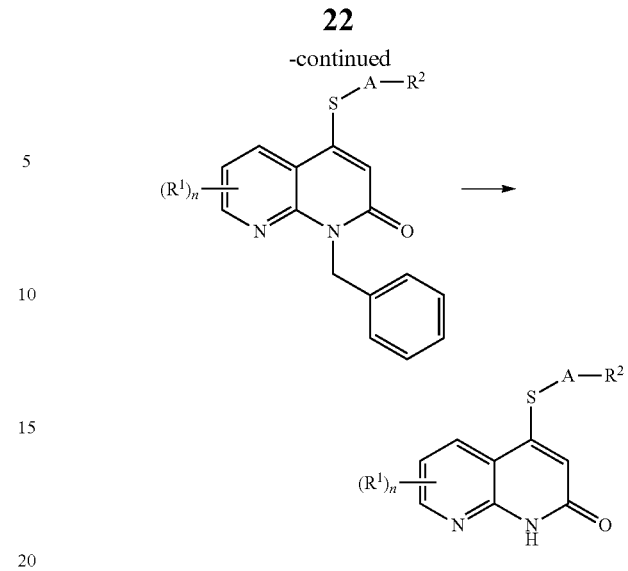

A6 may be treated with a thiol (HS-A-$R^2$) in the presence of an appropriate base. The base may be selected from amine bases, hydroxide salts (non-limiting examples include sodium hydroxide and tetraalkylamonium hydroxides), carbonate salts, hydrides, alkoxide salts (non-limiting examples include sodium methoxide and potassium t-butoxide) and the like.

It may be advantageous to employ a temporary protecting group in achieving the final product. The phrase "protecting group" as used herein means temporary modifications of a potentially reactive functional group which protect it from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, 2$^{nd}$ ed.; Wiley: New York, 1991).

The compounds and processes disclosed herein are useful in the production of a library of 4-thio substituted quinoline and naphthyridine derivatives for biological screening. Derivatives of quinoline and naphthyridine posses a range of biological activities. Quinoline-based compounds have shown efficacy, for example, as antivirals. Particularly, the compounds of the present invention may be used to prevent or treat infection with HCV.

The HCV Replicon Assay may be used to predict compound efficacy in treatment and/or prevention of HCV infection as well as inhibition of HCV replication and/or proliferation. The HCV Replicon encompasses a multiplicity of viral and host targets through which an inhibitor could work to inhibit HCV Replication. Viral targets expressed in the HCV Replicon include the HCV IRES (for translation), NS3 Protease, the HCV Helicase/ATPase, NS5A phosphorylation, and the NS5B polymerase. Without being limited to theory, it is believed that the compounds of the present invention inhibit HCV replication. The compounds of the invention may inhibit replication as by acting on the IRES, NS3 protease, NS5B polymerase, Helicase/ATPase, or NS5A phosphorylation.

Expression of HCV IRES driven luciferase reporter activity and HCV RNA is measured to obtain indirect and direct measures of replication of HCV RNA respectively. Inhibitors of HCV replication and/or proliferation are determined by initially identifying molecules that inhibit expression of the HCV IRES driven luciferase reporter in this HCV Replicon Luciferase Assay. Cell viability assays and control cell based luciferase assays are then run on hits identified in the HCV Replicon Luciferase Assay to eliminate cytoxic compounds and non-specific compounds which act by inhibiting the luciferase enzyme. Validated inhibitors of HCV replication and/or proliferation are identified by evaluating HCV Replicon Luciferase hits that are specific and non-cytoxic and demonstrating that these compounds inhibit expression of HCV RNA using a quantitative PCR based approach (Taqman) using primers and probes specific for HCV RNA (HCV Replicon RNA Assay).

Thus, in another embodiment, the present invention provides pharmaceutical compositions comprising an anti-HCV effective amount of a compound of formula I, or a pharmaceutically acceptable salt or hydrate thereof, in combination with a pharmaceutically acceptable carrier or auxiliary agent. As used herein, the terms "pharmaceutically acceptable salts" and "hydrates" refer to those salts and hydrated forms of the compound that would favorably affect the physical or pharmacokinetic properties of the compound, such as solubility, palatability, absorption, distribution, metabolism and excretion. Other factors, more practical in nature, which those skilled in the art may take into account in the selection include the cost of the raw materials, ease of crystallization, yield, stability, solubility, hygroscopicity and flowability of the resulting bulk drug.

The invention also provides a method of treating HCV infection in a mammal, preferable a human, by administering to the mammal an effective amount of a compound of the present invention, a pharmaceutically acceptable salt or hydrate thereof, or a composition as described above. The compounds of the invention may be administered alone or may be administered in combination with other approved therapeutics, such as: an interferon (pegylated or not), preferably α-interferon, ribavirin, or interferon and ribavirin, or one or more other anti-HCV agent, such as an HCV protease inhibitor, HCV polymerase inhibitor, HCV IRES inhibitor, HCV Helicase and/or ATPase inhibitor, NS5A phosphorylation inhibitor, HCV NS2 inhibitor, or other HCV life cycle inhibitor. Combination therapies with may include a compound of the invention with multiple different inhibitors of HCV life cycle (immunomodulatory agents, Toll Like Receptor modulators, antisense therapeutics etc.). The agents that comprise a combination therapy may be administered together or separately, e.g., prior to, concurrently with or following the administration of the compound of the invention or pharmaceutically acceptable salt thereof. These additional agents may be combined with the compounds of this invention to create a single pharmaceutical dosage form. Alternatively these additional agents may be separately administered to the patient as part of a multiple dosage form, for example, using a kit. Such additional agents may be administered to the patient prior to, concurrently with, or following the administration of a compound of formula (I), or a pharmaceutically acceptable salt thereof.

The compounds of the present invention may be employed in solid or liquid form including, for example, amorphous powder or crystalline form, in solution or in suspension. They may be administered in numerous different ways, such as orally, parenterally, topically, transdermally or by inhalation. Oral administration or administration by injection is preferred. The choice of carrier and the content of active compound in the carrier are generally determined in accordance with the solubility and chemical properties of the desired product, the particular mode of administration and well established pharmaceutical practice. The pharmaceutical composition of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intra-articular, intrasynovial, intrasternal, intrathecal, and intralesional injection or infusion techniques.

Examples of liquid carriers include syrups, peanut oil, olive oil, water, saline and the like. For parenteral administration, emulsions, suspensions or solutions of the compounds according to the invention in vegetable oil, for example sesame oil, groundnut oil or olive oil, or aqueous-organic solutions such as water and propylene glycol, injectable organic esters such as ethyl oleate, as well as sterile aqueous solutions of the pharmaceutically acceptable salts, may be used. Injectable forms must be fluid to the extent they can be easily syringed, and proper fluidity can be maintained, for example, by the use of a coating such as lecithin, by the maintenance of the required particle size in the case of dispersion and by the use of surfactants. Prolonged absorption of the injectable compositions can be brought about by use of agents delaying absorption, for example, aluminum monostearate and gelatin. The pharmaceutical composition may be in the form of a sterile injectable preparation, for example, as a sterile injectable aqueous or oleaginous suspension. This suspension may be formulated according to techniques known in the art using suitable dispersing or wetting agents (such as, for example Tween 80) and suspending agents.

The pharmaceutical composition of this invention may be orally administered in any orally acceptable dosage form including, but not limited to, capsules, tablets, and aqueous suspensions and solutions. Compounds of the invention may be enclosed in hard or soft shell gelatin capsules, or compressed into tablets. Examples of oral liquid dosage forms include solutions, suspensions, syrups, emulsions, soft gelatin capsules and the like. Carriers for oral use (solid or liquid) may include time delay materials known in the art, such as glyceryl monostearate or glyceryl distearate alone or with a wax. To prepare a capsule, it may be advantageous to use lactose and a liquid carrier, such as high molecular weight polyethylene glycols.

Compositions and dosage forms prepared in accordance with the present invention optionally may contain lactose, sodium citrate, calcium carbonate, dicalcium phosphate and disintegrating agents such as starch, alginic acids and certain complex silica gels combined with lubricants such as magnesium stearate, sodium lauryl sulfate and talc may be used for preparing tablets, capsules and the like. Various other materials may be present as coatings or to otherwise modify the physical form of the dosage unit. For instance, tablets, and capsules may be coated with shellac, sugar or both. When aqueous suspensions are used they may contain emulsifying agents or agents which facilitate suspension. Diluents such as sucrose, ethanol, polyols such as polyethylene glycol, propylene glycol and glycerol, and mixtures thereof also may be used. In addition, the active compound may be incorporated into sustained-release preparations and formulations. If desired, certain sweetening and/or flavoring and/or coloring agents may be added. Other suitable vehicles or carriers for the above noted formulations and compositions can be found in standard pharmaceutical texts, e.g. in "Remington's Pharmaceutical Sciences", The Science and Practice of Pharmacy, 19.sup.th Ed. Mack Publishing Company, Easton, Pa., (1995).

When these compounds or their pharmaceutically acceptable salts are formulated together with a pharmaceutically acceptable carrier, the resulting composition may be administered in vivo to mammals, such as man, to treat or prevent HCV virus infection. Such treatment may also be achieved using a compound of this invention in combination with other anti-viral agents which include, but are not limited to a-interferon and ribavirin. The additional agents may be combined with compounds of this invention to create a single dosage form. Alternatively these additional agents may be separately administered to a mammal as part of a multiple dosage form.

EXAMPLES

General Methods

Reaction solvents were commercially purchased from Acros and Aldrich without further purification and reagents were used as received. Reactions for the synthesis of the starting material were monitored by thin-layer chromatography (TLC) on 0.25 mm precoated Merck Silica Gel 60 $F_{254}$, visualizing with ultraviolet light or phosphomolybdic acid stain. Flash column chromatography was performed on Merck Silica Gel 60 (230-400 mesh) using reagent grade hexanes, dichloromethane, methanol and ethyl acetate.

Reaction reagents were commercially purchased from Alrich and used as received. $^1$H and $^{13}$C NMR spectra were recorded on a Varian 500 MHz spectrometer and are referenced to residual solvent peaks or to an internal reference of tetramethylsilane in $CDCl_3$. LC-MS were obtained on a Micromass ZQ mass spectrometer in ES+ mode with a Water 2790 HPLC system. HPLC condition: C18 column (3.5 μm, 2.1×50 mm, W93491F 26) using a flow rate of 0.4 mL/min in a gradient of 15-100% $CH_3CN$ in H2O in 9 min with 1 min wash.

Example 1

2,4-Dichloroquinoline 2

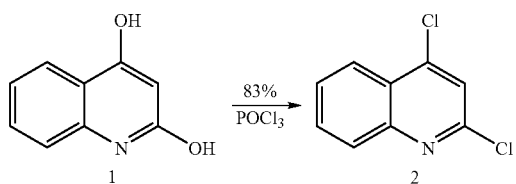

A mixture of 2,4-quinolinediol (13.6 g, 84.47 mmol) in $POCl_3$ (150 mL) was heated under reflux for 3 h. After cooling down, the mixture was dropped slowly into crashed ice while shaking. The precipitate was collected by filtration and washed several times with water. The product was dried under vacuum overnight to give 13.86 g (yield 83%) of product as pale gray powder which is pure enough for further use. $^1$H NMR (500 MHz, $CDCl_3$) δ 8.17 (d, J=8.0 Hz, 1H), 8.02 (d, J=8.0 Hz, 1H), 7.79 (t, J=8.0 Hz, 1H), 7.64 (t, J=8.0 Hz, 1H), 7.49 (s, 1H);

$^{13}$C NMR (125 MHz, $CDCl_3$) 150.06, 148.33, 144.62, 131.79, 129.20, 128.13, 125.39, 124.42, 122.19; LCMS (EI) m/z 198.0 (M+), 200.0, 202.0.

Example 2

General Procedure for 2,4-Dichloroquinolines

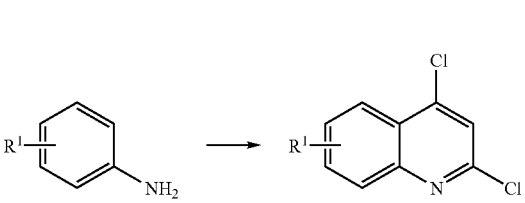

To a suspension of malonic acid (100 mmol) in $POCl_3$ (100 mL) was added aniline or substituted aniline in portions. The mixture was heated at 110° C. for 1 hr and 140° C. for another 4 hr. After cooling, the mixture was poured slowly into crushed ice while shaking. The mixture was allowed to stand in a refrigerator overnight before filtration. The precipitate was collected, washed several times with water and dried under vacuum. $CH_2Cl_2$ was used to extract the solid. The extract was dried and purified on column to give 2,4-dichloroquinoline or substituted 2,4-dichloroquinoline in yields of approximately 70%.

2,4-Dichloro-quinoline

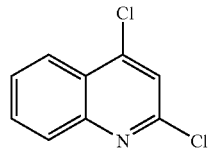

$^1$H NMR (500 MHz, $CDCl_3$) δ 8.17 (d, J=8.0 Hz, 1H), 8.02 (d, J=8.0 Hz, 1H), 7.79 (t, J=8.0 Hz, 1H), 7.64 (t, J=8.0 Hz, 1H), 7.49 (s, 1H); $^{13}$C NMR (125 MHz, $CDCl_3$) 150.06, 148.33, 144.62, 131.79, 129.20, 128.13, 125.39, 124.42, 122.19; LCMS (EI) m/z 198.0 (M+), 200.0, 202.0.

2,4-Dichloro-6-methyl-quinoline

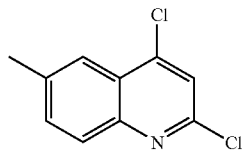

$^1$H NMR (500 MHz, CDCl$_3$) δ 7.96 (s, 1H), 7.93 (d, J=9.0 Hz, 1H), 7.63 (d, J=9.0 Hz, 1H), 7.49 (s, 1H), 2.59 (s, 3H); LCMS (EI) m/z 212.1 (M$^+$), 214.1, 216.1.

2,4-Dichloro-6-methoxy-quinoline

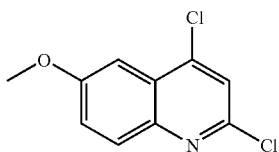

$^1$H NMR (500 MHz, CDCl$_3$) δ 7.93 (d, J=8.5 Hz, 1H), 7.49 (s, 1H), 7.43 (d, J=8.5 Hz, 1H), 7.41 (s, 1H), 3.98 (s, 3H); LCMS (EI) m/z 228.1 (M$^+$), 230.0, 232.1.

Example 3

General Procedure for 2-chloro-4-thioarylquinolines

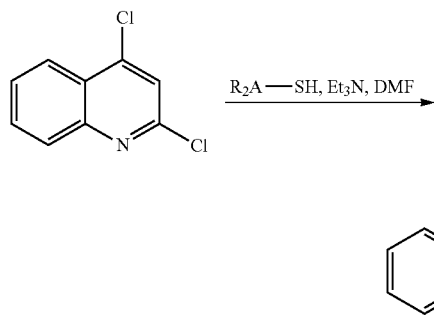

To a solution of 2,4-dichloroquinoline (1.98 g, 10.0 mmol) in DMF (10 mL) was added Et$_3$N (2.78 mL, 20 mmol) and a solution of thiol (10 mmol) in DMF (10 mL) dropwise at 0° C. The reaction was warmed up after 10 min and stirred overnight at rt. 200 mL of EtOAc was added to the mixture and washed with water and brine successively. The organic layer was separated and dried over Na$_2$SO$_4$. The product was purified on column after removal of solvent under vacuum. In most of cases, less than 5% of dithio-substituted quinoline was formed.

2-Chloro-4-(4-fluoro-phenylsulfanyl)-quinoline

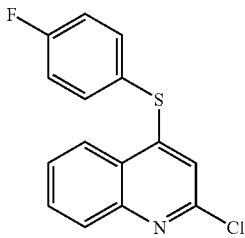

Yield: 62%. $^1$H NMR (500 MHz, CDCl$_3$) δ 8.13 (d, J=8.0 Hz, 1H), 7.99 (d, J=8.0 Hz, 1H), 7.75 (t, J=8.0 Hz, 1H), 7.62-7.57 (m, 3H), 7.23 (t, J=8.0 Hz, 2H), 6.57 (s, 1H);

$^{13}$C NMR (125 MHz, CDCl$_3$) 165.32, 163.31, 152.47, 150.65, 147.26, 138.29, 138.22, 131.24, 129.36, 127.09, 124.52, 123.41, 118.09, 117.91, 117.32; LCMS (EI) m/z 289.9 (M$^+$), 291.9, 293.0.

2-Chloro-4-(4-chloro-phenylsulfanyl)-quinoline

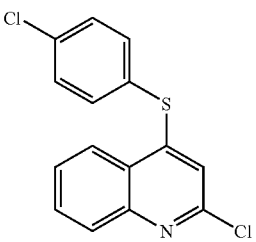

Yield: 85%. $^1$H NMR (500 MHz, CDCl$_3$) δ 8.15 (d, J=8.0 Hz, 1H), 8.01 (d, J=8.0 Hz, 1H), 7.77 (t, J=8.0 Hz, 1H), 7.61 (t, J=8.0 Hz, 1H), 7.55 (d, J=8.5 Hz, 2H), 7.51 (d, J=8.5 Hz, 2H), 6.66 (s, 1H); $^{13}$C NMR (125 MHz, CDCl$_3$) 151.69, 150.63, 147.36, 137.10, 137.00, 131.30, 130.89, 129.41, 127.19, 127.04, 124.67, 123.52, 117.89; LCMS (EI) m/z 305.9 (M$^+$), 307.9, 309.9.

2-Chloro-4-(4-methyl-phenylsulfanyl)-quinoline

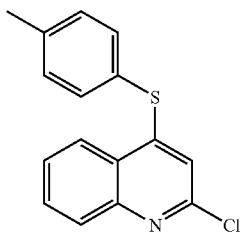

Yield: 63%. $^1$H NMR (500 MHz, CDCl$_3$) δ 8.17 (d, J=8.0 Hz, 1H), 7.99 (d, J=8.0 Hz, 1H), 7.75 (t, J=8.0 Hz, 1H), 7.59 (t, J=8.0 Hz, 1H), 7.50 (d, J=8.0 Hz, 2H), 7.34 (d, J=8.0 Hz, 2H), 6.62 (s, 1H); $^{13}$C NMR (125 MHz, CDCl$_3$) 153.24, 150.71, 147.24, 141.13, 136.01, 131.43, 131.09, 129.30, 126.94, 124.65, 124.50, 123.52, 117.26, 21.68; LCMS (EI) m/z 285.9 (M$^+$), 287.9.

2-Chloro-4-(4-methoxy-phenylsulfanyl)-quinoline

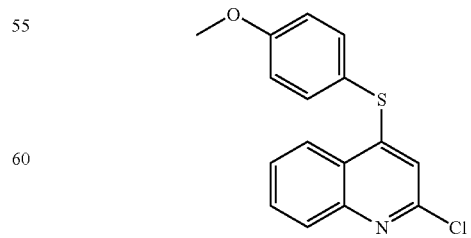

Yield: 66%. $^1$H NMR (500 MHz, CDCl$_3$) δ 8.16 (d, J=8.0 Hz, 1H), 7.99 (d, J=8.0 Hz, 1H), 7.15 (t, J=8.0 Hz, 1H), 7.59 (t, J=8.0 Hz, 1H), 7.54 (d, J=8.0 Hz, 2H), 7.06 (d, J=8.0 Hz, 2H), 6.57 (s, 1H); $^{13}$C NMR (125 MHz, CDCl$_3$) 161.71, 153.88, 150.74, 147.20, 137.90, 131.08, 129.28, 126.89, 124.53, 123.43, 118.13, 116.90, 116.24, 55.74; LCMS (EI) m/z 301.9 (M$^+$), 303.9.

2-Chloro-4-(4-bromo-phenylsulfanyl)-quinoline

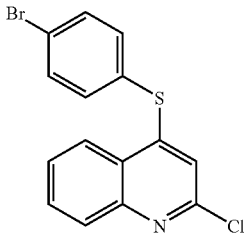

Yield: 80%. $^1$H NMR (500 MHz, CDCl$_3$) δ 8.15 (d, J=8.0 Hz, 1H), 8.01 (d, J=8.0 Hz, 1H), 7.77 (t, J=8.0 Hz, 1H), 7.66 (d, J=8.0 Hz, 2H), 7.60 (t, J=8.0 Hz, 1H), 7.47 (d, J=8.0 Hz, 2H), 6.68 (s, 1H); $^{13}$C NMR (125 MHz, CDCl$_3$) 151.47, 150.63, 147.36, 137.13, 133.84, 131.32, 129.41, 127.77, 127.21, 125.30, 124.69, 123.54, 118.01; LCMS (EI) m/z 349.8 (M$^+$), 351.7, 353.8.

2-Chloro-4-(4-amino-phenylsulfanyl)-quinoline

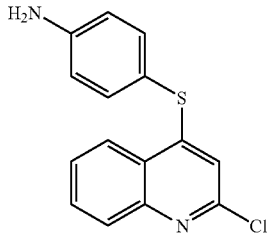

Yield: 63%. $^1$H NMR (500 MHz, CDCl$_3$) δ 8.16 (d, J=8.0 Hz, 1H), 7.98 (d, J=8.0 Hz, 1H), 7.74 (t, J=8.0 Hz, 1H), 7.58 (t, J=8.0 Hz, 1H), 7.39 (d, J=8.0 Hz, 2H), 6.81 (d, J=8.0 Hz, 2H), 6.60 (s, 1H); $^{13}$C NMR (125 MHz, CDCl$_3$) 154.70, 150.80, 148.92, 147.16, 137.86, 130.98, 129.22, 126.77, 124.55, 123.44, 116.71, 116.70, 114.40; LCMS (EI) m/z 286.9 (M$^+$), 288.9.

2-Chloro-4-(4-trifluoromethyl-phenylsulfanyl)-quinoline

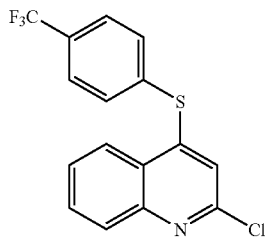

Yield: 85%. $^1$H NMR (500 MHz, CDCl$_3$) δ 8.17 (d, J=8.5 Hz, 1H), 8.04 (d, J=8.5 Hz, 1H), 7.79 (t, J=8.5 Hz, 1H), 7.74 (d, J=8.5 Hz, 2H), 7.67 (d, J=8.5 Hz, 2H), 7.62 (t, J=8.5 Hz, 1H), 6.85 (s, 1H); $^{13}$C NMR (125 MHz, CDCl$_3$) 150.56, 149.62, 147.61, 134.69, 134.63, 131.47, 129.52, 127.50, 127.28, 127.25, 127.22, 127.20, 125.31, 123.84, 119.76; LCMS (EI) m/z 339.8 (M$^+$), 341.8, 342.9.

4-(4-tert-Butyl-phenylsulfanyl)-2-chloro-quinoline

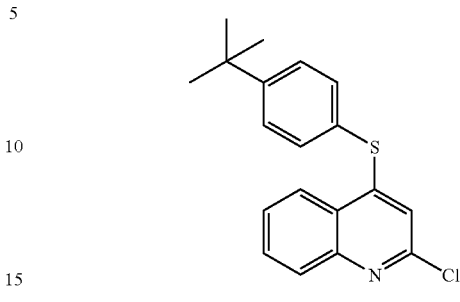

Yield: 52%. $^1$H NMR (500 MHz, CDCl$_3$) δ 8.19 (d, J=8.0 Hz, 1H), 7.99 (d, J=8.0 Hz, 1H), 7.75 (t, J=8.0 Hz, 1H), 7.59 (t, J=8.0 Hz, 1H), 7.55 (bs, 4H), 6.67 (s, 1H); $^{13}$C NMR (125 MHz, CDCl$_3$) 154.14, 153.09, 150.69, 147.26, 135.71, 131.10, 129.30, 127.72, 126.95, 124.69, 124.57, 123.56, 117.37, 35.20, 31.45; LCMS (EI) m/z 327.9 (M$^+$), 329.9, 331.0.

4-Benzylsulfanyl-2-chloro-quinoline

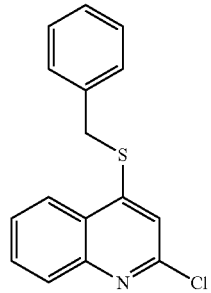

Yield: 71%. $^1$H NMR (500 MHz, CDCl$_3$) δ 8.05 (d, J=8.0 Hz, 1H), 7.98 (d, J=8.0 Hz, 1H), 7.72 (t, J=8.0 Hz, 1H), 7.53 (t, J=8.0 Hz, 1H), 7.45 (d, J=7.0 Hz, 2H), 7.38 (t, J=7.5 Hz, 2H), 7.33 (t, J=7.5 Hz, 1H), 7.18 (s, 1H); $^{13}$C NMR (125 MHz, CDCl$_3$) 151.02, 150.45, 147.08, 134.69, 131.04, 129.38, 129.25, 129.21, 128.33, 126.90, 125.09, 123.63, 116.58, 36.45; LCMS (EI) m/z 285.9 (M$^+$), 287.9.

Example 4

General Procedure for Substituted 4-chloro-1-methyl-1H-quinolin-2-ones

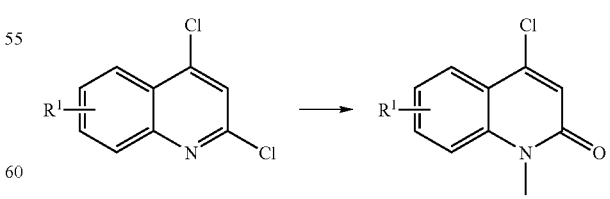

To a solution of optionally substituted 2,4-dichloroquinoline (10.0 mmol) in 1,4-dioxane (20 mL) was added HCl (6 N, 30 mL). The mixture was refluxed overnight. After cooling, 200 mL of water was added and precipitate was formed. The precipitate was collected and dried under vacuum. To the dry solid was added anhydrous acetone (50 mL), K$_2$CO$_3$ (2 equiv.) and MeI (5 equiv.). The mixture was heated to reflux overnight. The insoluble solid was filtered off and the solution was dried and purified on a column. The yields were around 50% for the two steps.

4-Chloro-1,6-dimethyl-1H-quinolin-2-one

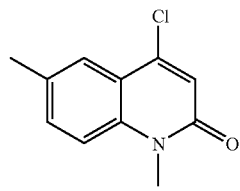

$^1$H NMR (500 MHz, CDCl$_3$) δ 7.81 (s, 1H), 7.46 (d, J=8.5 Hz, 1H), 7.30 (d, J=8.5 Hz, 1H), 6.88 (s, 1H), 3.70 (s, 3H) 2.47 (s, 3H); LCMS (EI) m/z 208.1 (M$^+$), 210.2.

4-Chloro-6-methoxy-1-methyl-1H-quinolin-2-one

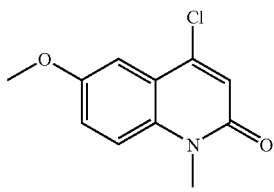

$^1$H NMR (500 MHz, CDCl$_3$) δ 7.42 (d, J=2.5 Hz, 1H), 7.33 (d, J=9.0 Hz, 1H), 7.24 (dd, J=9.0, 2.5 Hz, 1H), 6.90 (s, 1H), 3.90 (s, 3H) 3.69 (s, 3H); LCMS (EI) m/z 224.2 (M$^+$), 226.2.

Example 5

General Procedure for 4-(phenylsulfanyl)-1-methyl-1H-quinolin-2-ones

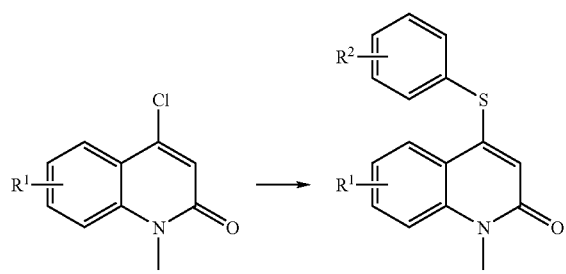

To a solution of 4-chloro-1-methyl-1H-quinolin-2-one or substituted 4-chloro-1-methyl-1H-quinolin-2-one (1 mmol) and 4-aminophenylthiol (1.5 mmol) in DMF (5 mL) was added NaOH (10 N, 1.5 mmol). The reaction was stirred at rt overnight. 50 mL of H$_2$O was added to the mixture. The precipitate was collected and purified on a column to give the product in around 90% yield.

4-(4-Amino-phenylsulfanyl)-1-methyl-1H-quinolin-2-one

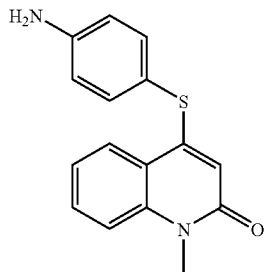

$^1$H NMR (500 MHz, CDCl$_3$) δ 8.00 (d, J=8.0 Hz, 1H), 7.59 (t, J=8.0 Hz, 1H), 7.36 (d, J=8.0 Hz, 1H), 7.32 (d, J=8.0 Hz, 2H), 7.27 (t, J=8.0 Hz, 1H), 6.73 (d, J=8.0 Hz, 2H), 6.04 (s, 1H), 3.99 (s, 2H), 3.65 (s, 3H); $^{13}$C NMR (125 MHz, CDCl$_3$) 161.43, 153.18, 148.91, 139.23, 137.97, 131.19, 124.69, 122.07, 119.42, 116.51, 115.16, 114.68, 114.31, 29.47; LCMS (EI) m/z 283.0 (M$^+$), 284.0.

4-(4-Amino-phenylsulfanyl)-1,6-dimethyl-1H-quinolin-2-one

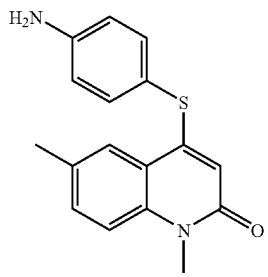

$^1$H NMR (500 MHz, CDCl$_3$) δ 7.79 (s, 1H), 7.41 (d, J=8.5 Hz, 1H), 7.33 (d, J=8.0 Hz, 2H), 7.26 (d, J=8.0 Hz, 1H), 6.74 (d, J=8.0 Hz, 2H), 6.02 (s, 1H), 3.98 (s, 2H), 3.64 (s, 3H), 2.47 (s, 3H); LCMS (EI) m/z 297.2 (M$^+$), 298.2.

4-(4-Amino-phenylsulfanyl)-6-methoxy-1-methyl-1H-quinolin-2-one

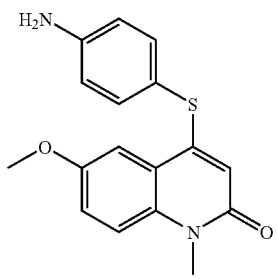

$^1$H NMR (500 MHz, CDCl$_3$) δ 7.42 (s, 1H), 7.32 (d, J=8.0 z, 2H), 7.30 (d, J=8.5 Hz, 1H), 7.21 (d, J=8.5 Hz, 1H), 6.74 (d,

J=8.0 Hz, 2H), 6.07 (s, 1H), 3.99 (s, 2H), 3.91 (s, H), 3.64 (s, 3H); LCMS (EI) m/z 313.1 (M⁺), 314.2.

Example 6

4-(4-Fluoro-phenylsulfanyl)-1H-quinolin-2-one

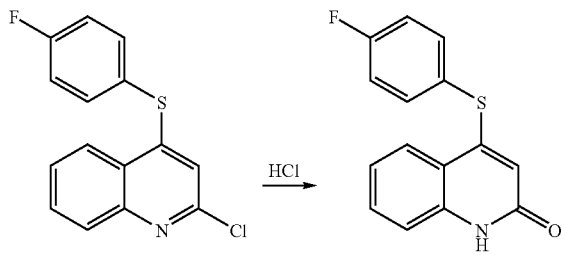

A solution of 2-chloro-4-(4-fluoro-phenylsulfanyl)-quinoline (145 mg, 0.50 mmol) in TFA (2 mL) and HCl (6 N, 2 mL) was heated under microwave radiation at 120° C. for 20 min. After cooling down, 20 mL of water was added. The precipitate was collected by filtration and washed with water for several times. The product was air dried (115 mg, 85%) and was pure enough without further purification. Note: the solubility of the product in organic solvent is very poor. ¹H NMR (500 MHz, DMSO-d6) δ 11.6 (bs, 1H), 7.82 (d, J=8.0 Hz, 1H), 7.71 (m, 2H), 7.56 (t, J=8.0 Hz, 1H), 7.43 (m, 3H), 7.33 (d, J=8.0 Hz, 1H), 7.23 (t, J=8.0 Hz, 1H), 5.56 (s, 1H); LCMS (EI) m/z 272.0 (M⁺), 273.0.

Example 7

1-Benzyl-4-chloro-1H-[1,8]naphthyridin-2-one and 2,4-Dichloro-[1,8]naphthyridine

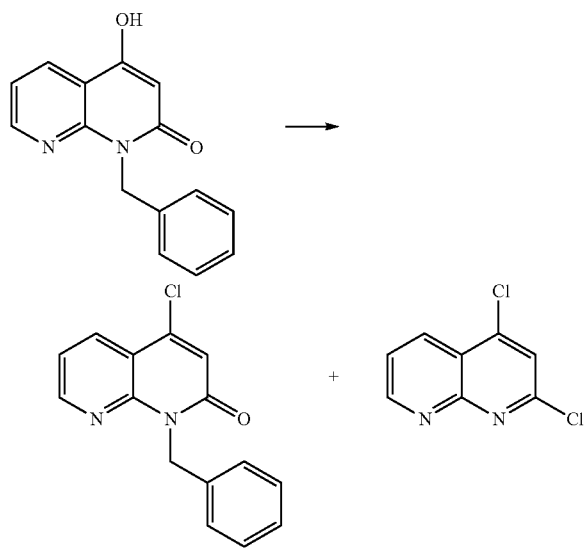

A mixture of 1-benzyl-4-hydroxy-1H-[1,8]naphthyridin-2-one (2.52 g, 10 mmol) in POCl₃ (100 mL) was heated under reflux for 2 h. After cooling down, the reaction mixture was dropped to crashed ice while shaking. The solution was neutralized with NaOH followed by extraction with EtOAc. The organic layer was separated, washed with brine and dried over Na₂SO₄. The products were purified on column after removal of solvent under vacuum to give 1-benzyl-4-chloro-1H-[1,8] naphthyridin-2-one (1.26 g, yield: 47%) and 2,4-dichloro-[1,8]naphthyridine (556 mg, 28%). 1-Benzyl-4-chloro-1H-[1,8] naphthyridin-2-one: ¹H NMR (500 MHz, CDCl₃) δ 8.64 (d, J=3.0 Hz, 1H), 8.22 (d, J=7.0 Hz, 1H), 7.49 (d, J=7.0 Hz, 2H), 7.21-7.28 (m, 4H), 6.94 (s, 1H), 5.73 (s, 2H); ¹³C NMR (125 MHz, CDCl₃) 161.62, 151.31, 149.38, 143.20, 137.49, 134.57, 128.92, 128.55, 127.58, 122.40, 118.80, 115.00, 44.56; LCMS (EI) m/z 270.9 (M⁺), 273.0. 2,4-Dichloro-[1,8]naphthyridine: ¹H NMR (500 MHz, CDCl₃) δ 9.10 (d, J=3.0 Hz, 1H), 8.51 (d, J=8.5 Hz, 1H), 7.57 (dd, J=8.5, 3.0 Hz, 1H), 7.54 (s, 1H); ¹³C NMR (125 MHz, CDCl₃) 155.63, 155.39, 153.62, 144.70, 133.97, 123.38, 123.36, 120.69; LCMS (EI) m/z 198.9 (M⁺), 200.7, 203.0.

Example 8

1-Benzyl-4-(4-bromo-phenylsulfanyl)-1H-[1,8]naphthyridin-2-one

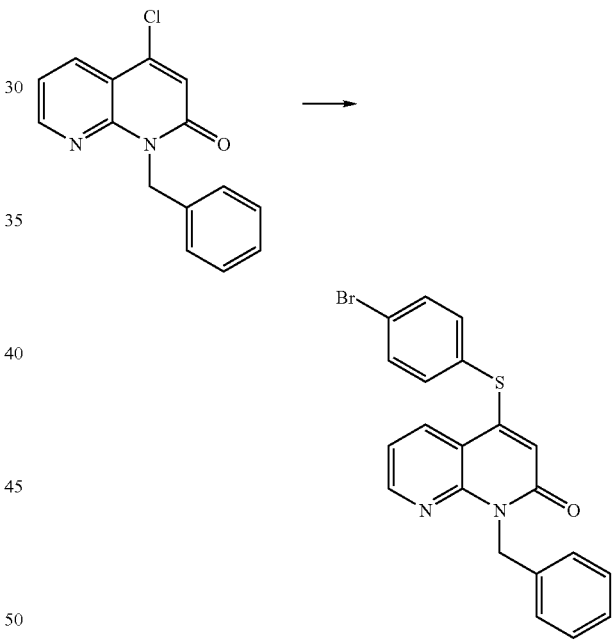

To a suspension of NaH (24 mg, 1 mmol) in DMF (4 mL) was added 4-bromobenzenethiol (189 mg, 1 mmol) at 0° C. After being stirred at rt for 10 min, a solution of 1-benzyl-4-chloro-1H-[1,8]naphthyridin-2-one (135 mg, 0.5 mmol) in DMF (1 mL) was introduced at rt. The reaction was quenched by adding water followed by extracting with EtOAc. The organic layer was washed with brine and dried over Na₂SO₄. Column chromatography of the concentrated residue gave 210 mg of product (yield: 100%): ¹H NMR (500 MHz, CDCl₃) δ 8.63 (d, J=5.0 Hz, 1H), 8.21 (d, J=8.0 Hz, 1H), 7.62 (d, J=8.5 Hz, 2H), 7.46 (d, J=7.5 Hz, 2H), 7.43 (d, J=8.5 Hz, 2H), 7.25 (t, J=7.5 Hz, 2H), 7.21 (dd, J=8.0, 5.0 Hz, 1H), 7.20 (t, J=8.0 Hz, 1H), 6.10 (s, 1H), 5.70 (s, 2H); ¹³C NMR (125 MHz, CDCl₃) 161.65, 150.77, 149.42, 148.87, 137.85, 137.46, 133.78, 132.97, 128.82, 128.47, 127.38, 126.81, 125.50, 118.09, 117.66, 114.65, 44.20; LCMS (EI) m/z 422.8 (M⁺), 424.8.

Example 9

4-(4-Bromo-phenylsulfanyl)-1H-[1,8]naphthyridin-2-one

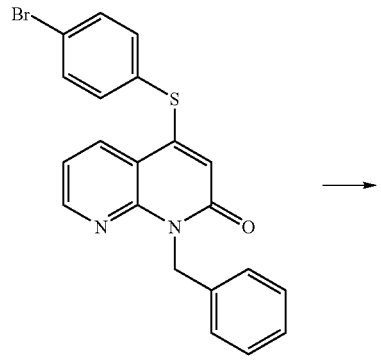

A mixture of 1-benzyl-4-(4-bromo-phenylsulfanyl)-1H-[1,8]naphthyridin-2-one (200 mg, 0.47 mmol) and HBr (5 mL, 48%) was heated under reflux for 4 h. After cooling, water was added and the mixture was neutralized with NaOH. The mixture was extracted with EtOAc. The organic layer was washed with brine and dried over Na₂SO₄. After removal of solvent, the solid was recrystallized with EtOAc and hexane to give 30 mg of product (Yield: 19%). Note: the solubility of the product in organic solvent is poor. ¹H NMR (500 MHz, DMSO-d6) δ 12.12 (s, 1H), 8.58 (d, J=4.0 Hz, 1H), 8.22 (d, J=8.0 Hz, 1H), 7.76 (d, J=8.0 Hz, 2H), 7.58 (d, J=8.0 Hz, 2H), 7.29 (dd, J=8.0, 5.0 Hz, 1H), 5.74 (s, 1H); LCMS (EI) m/z 332.8 (M⁺), 334.9.

Example 10

4-Chloro-1-methyl-1H-[1,8]naphthyridin-2-one

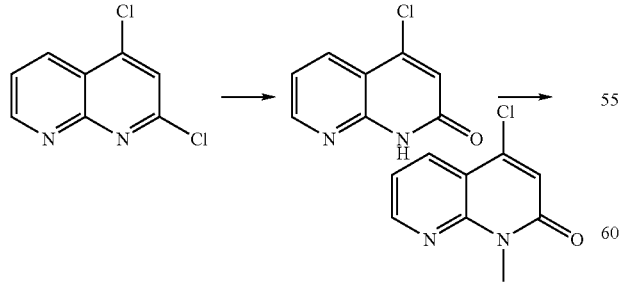

A solution of 2,4-dichloro-[1,8]naphthyridine (556 mg, 2.79 mmol) in 1,4-dioxane (20 mL) and HCl (6N, 20 mL) was heated under reflux overnight. After cooling down, the reaction was neutralized with NaOH solution. The precipitate was collected by filtration and washed with water for several times. The product was air dried to give 400 mg of product and it was used for the next step without further purification. To a suspension of 4-chloro-1H-[1,8]naphthyridin-2-one obtained above in DMF (20 mL) was added NaH (64 mg) in portion at rt. After 20 min, MeI (0.27 mL, 4.4 mmol) was added and stirred overnight at rt. The reaction was quenched by adding water, extracting with EtOAc. The organic layer was washed once again with brine and dried over Na₂SO₄. The product (300 mg, 55% for 2 steps) was purified by column chromatography after being concentrated under vacuum. ¹H NMR (500 MHz, CDCl₃) δ 8.67 (d, J=4.5 Hz, 1H), 8.27 (d, J=8.0 Hz, 1H), 7.28 (dd, J=8.0, 4.5 Hz, 1H), 6.94 (s, 1H); ¹³C NMR (125 MHz, CDCl₃) 161.94, 151.23, 149.80, 142.96, 134.55, 122.16, 118.57, 115.04, 28.84; LCMS (EI) m/z 198.9 (M⁺), 200.7, 203.0.

Example 11

General procedure for
4-thioary-1-methyl-1H-[1,8]naphthyridin-2-ones

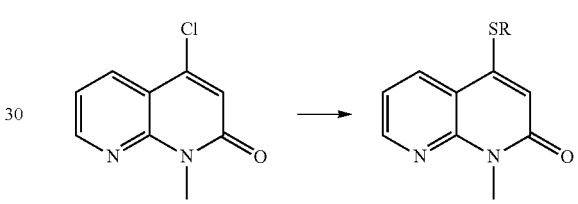

To a suspension of NaH (12 mg, 0.5 mmol) in DMF (2 mL) was added dropwise a solution of thiols (0.5 mmol) in DMF (1 mL) at rt. After 10 min, 4-chloro-1-methyl-1H-[1,8]naphthyridin-2-one (49 mg, 0.25 mmol) was added. The reaction was quenched by adding water followed by extracting with EtOAc. The organic layer was washed with brine and dried over Na₂SO₄. Column chromatography of the concentrated residue gave products in yields vary from 57% to 85%.

4-(4-Fluoro-phenylsulfanyl)-1-methyl-1H-[1,8]naphthyridin-2-one

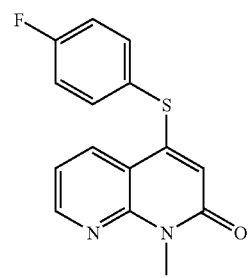

Yield: 85%. ¹H NMR (500 MHz, CDCl₃) δ 8.64 (m, 1H), 8.23 (m, 1H), 7.56 (m, 2H), 7.27-7.17 (m, 3H), 6.02 (s, 1H), 3.76 (s, 3H); ¹³C NMR (125 MHz, CDCl₃) 165.36, 163.35, 162.03, 150.63, 149.88, 149.25, 138.41, 138.33, 132.85, 122.80, 117.99, 117.85, 117.81, 116.93, 114.63, 28.51; LCMS (EI) m/z 286.9 (M⁺), 288.0.

4-(4-Chloro-phenylsulfanyl)-1-methyl-1H-[1,8]naphthyridin-2-one

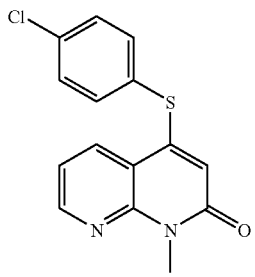

Yield: 85%. $^1$H NMR (500 MHz, CDCl$_3$) δ 8.64 (d, J=5.0 Hz, 1H), 8.22 (d, J=8.0 Hz, 1H), 7.49 (d, J=8.0 Hz, 2H), 7.45 (d, J=8.0 Hz, 2H), 7.21 (dd, J=8.0, 5.0 Hz, 1H), 6.08 (s, 1H), 3.76 (s, 3H); $^{13}$C NMR (125 MHz, CDCl$_3$) 161.98, 150.68, 149.28, 149.21, 137.20, 137.17, 132.95, 130.80, 126.26, 117.89, 117.52, 114.66, 28.54; LCMS (EI) m/z 302.9 (M$^+$), 304.9.

4-(4-Bromo-phenylsulfanyl)-1-methyl-1H-[1,8]naphthyridin-2-one

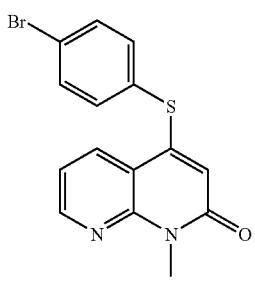

Yield: 57%. $^1$H NMR (500 MHz, CDCl$_3$) δ 8.65 (d, J=5.0 Hz, 1H), 8.22 (d, J=8.0 Hz, 1H), 7.61 (d, J=8.5 Hz, 2H), 7.42 (d, J=8.5 Hz, 2H), 7.22 (dd, J=8.0, 5.0 Hz, 1H), 6.09 (s, 1H), 3.77 (s, 3H); $^{13}$C NMR (125 MHz, CDCl$_3$) 161.98, 150.69, 149.30, 149.03, 137.31, 133.77, 132.99, 126.97, 125.42, 117.91, 117.67, 114.68, 28.56; LCMS (EI) m/z 346.8 (M$^+$), 348.9.

4-(4-Amino-phenylsulfanyl)-1-methyl-1H-[1,8]naphthyridin-2-one

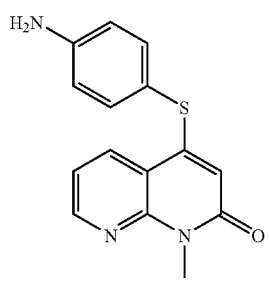

Yield: 72%. $^1$H NMR (500 MHz, CDCl$_3$) δ 8.63 (d, J=4.0 Hz, 1H), 8.26 (d, J=8.0 Hz, 1H), 7.32 (d, J=8.0 Hz, 2H), 7.21 (dd, J=8.0, 4.5 Hz, 1H), 6.75 (d, J=8.0 Hz, 2H), 6.07 (s, 1H), 3.98 (s, 2H), 3.76 (s, 3H); $^{13}$C NMR (125 MHz, CDCl$_3$) 162.30, 151.79, 150.35, 149.23, 149.01, 137.91, 132.80, 117.70, 116.56, 116.04, 114.84, 113.68, 28.44; LCMS (EI) m/z 284.0 (M$^+$), 285.1.

1-Methyl-4-p-tolylsulfanyl-1H-[1,8]naphthyridin-2-one

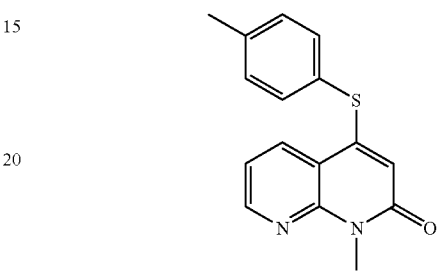

Yield: 79%. $^1$H NMR (500 MHz, CDCl$_3$) δ 8.62 (d, J=5.0 Hz, 1H), 8.24 (d, J=8.0 Hz, 1H), 7.44 (d, J=8.0 Hz, 2H), 7.28 (d, J=8.0 Hz, 2H), 7.20 (dd, J=8.0, 4.5 Hz, 1H), 6.04 (s, 1H), 3.75 (s, 3H), 2.41 (s, 3H); $^{13}$C NMR (125 MHz, CDCl$_3$) 162.15, 150.51, 150.45, 149.23, 141.16, 136.15, 132.89, 131.33, 123.81, 117,77, 116.70, 114.80, 28.47, 21.61; LCMS (EI) m/z 283.0 (M$^+$), 284.0.

Example 12

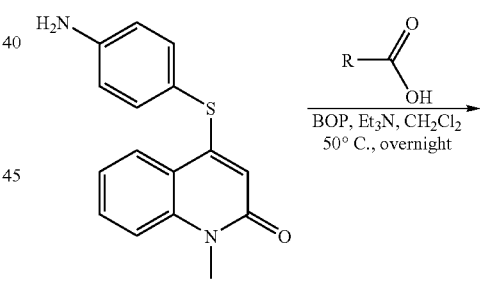

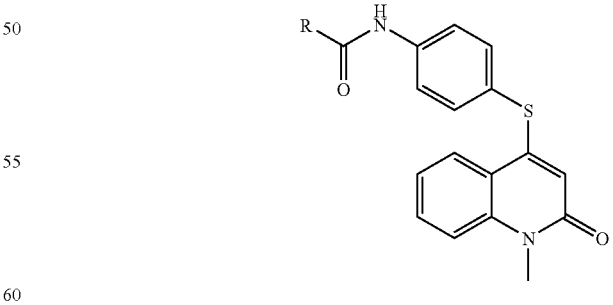

General procedure: To a solution of 4-(4-Amino-phenylsulfanyl)-1-methyl-1H-quinolin-2-one (1 mmol) and Acid (2 mmol) in CH$_2$Cl$_2$ (5 mL) was added Et$_3$N (3 mmol) and BOP (1.5 mmol). The reaction was stirred at 50° C. overnight. The mixture was purified on a column to give the product in around 70% yield.

39

N-[4-(1-Methyl-2-oxo-1,2-dihydro-quinolin-4-ylsulfanyl)-phenyl]-acetamide

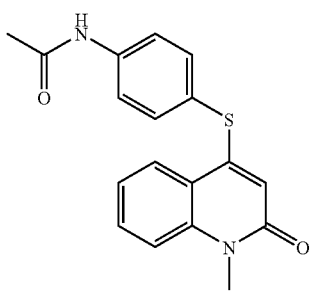

Yield: 90%. $^1$H NMR (500 MHz, CDCl$_3$) δ 8.53 (s, 1H), 8.01 (d, J=7.5 Hz, 1H), 7.66 (d, J=7.5 Hz, 2H), 7.64 (t, J=7.5 Hz, 1H), 7.49 (d, J=7.5 Hz, 2H), 7.40 (d, J=7.5 Hz, 1H), 7.31 (t, J=7.5 Hz, 1H), 6.01 (s, 1H), 3.69 (s, 3H), 2.21 (s, 3H); LCMS (EI) m/z 324.9 (M$^+$), 326.1.

2-Methoxy-N-[4-(1-methyl-2-oxo-1,2-dihydro-quinolin-4-ylsulfanyl)-phenyl]-acetamide

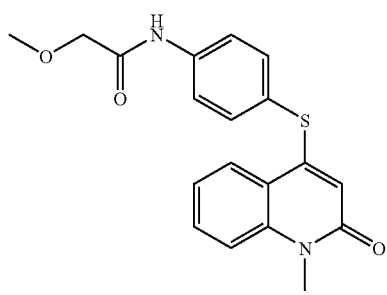

Yield: 90%. $^1$H NMR (500 MHz, CDCl$_3$) δ 8.39 (s, 1H), 8.00 (d, J=8.0 Hz, 1H), 7.73 (d, J=8.5 Hz, 2H), 7.62 (t, J=7.5 Hz, 1H), 7.55 (d, J=8.5 Hz, 2H), 7.38 (d, J=8.5 Hz, 1H), 7.29 (t, J=8.0 Hz, 1H), 6.03 (s, 1H), 4.06 (s, 2H), 3.67 (s, 3H), 3.55 (s, 3H); LCMS (EI) m/z 354.9 (M$^+$), 356.0.

2-(2-Methoxy-ethoxy)-N-[4-(1-methyl-2-oxo-1,2-dihydro-quinolin-4-ylsulfanyl)-phenyl]-acetamide

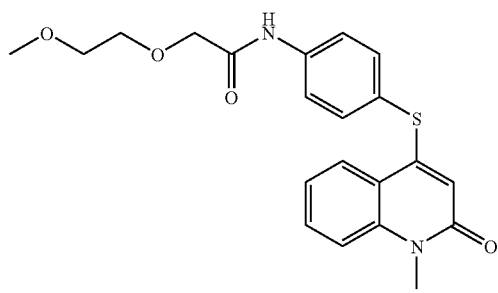

$^1$H NMR (500 MHz, CDCl$_3$) δ 9.12 (s, 1H), 8.01 (d, J=7.5 Hz, 1H), 7.74 (d, J=8.5 Hz, 2H), 7.62 (t, J=8.0 Hz, 1H), 7.55 (d, J=8.5 Hz, 2H), 7.38 (d, J=8.5 Hz, 1H), 7.29 (t, J=8.0 Hz, 1H), 6.03 (s, 1H), 4.15 (s, 2H), 3.80 (d, J=4.0 Hz, 2H), 3.67 (bs, 5H), 3.52 (s, 3H); LCMS (EI) m/z 398.9 (M$^+$), 400.1.

40

{[4-(1-Methyl-2-oxo-1,2-dihydro-quinolin-4-ylsulfanyl)-phenylcarbamoyl]-methyl}-carbamic acid tert-butyl ester

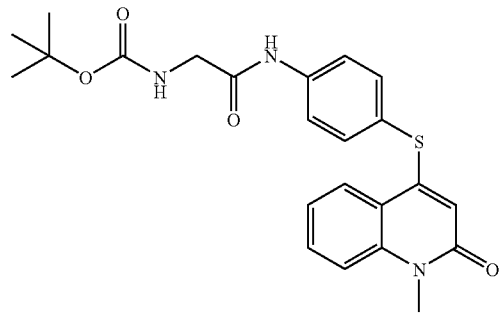

$^1$H NMR (500 MHz, CDCl$_3$) δ 8.87 (bs, 1H), 8.01 (d, J=7.5 Hz, 1H), 7.66 (d, J=8.5 Hz, 2H), 7.63 (t, J=8.0 Hz, 1H), 7.52 (d, J=8.0 Hz, 2H), 7.39 (d, J=8.5 Hz, 1H), 7.30 (t, J=8.0 Hz, 1H), 6.01 (s, 1H), 5.34 (bs, 1H), 3.97 (d, J=5.5 Hz, 2H), 3.68 (s, 3H), 1.50 (s, 9H); LCMS (EI) m/z 439.9 (M$^+$), 441.0.

2-[4-(1-Methyl-2-oxo-1,2-dihydro-quinolin-4-ylsulfanyl)-phenylcarbamoyl]-piperidine-1-carboxylic acid tert-butyl ester

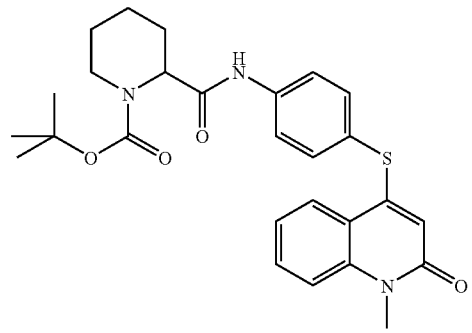

Yield: 55%. $^1$H NMR (500 MHz, CDCl$_3$) δ 8.58 (bs, 1H), 8.00 (d, J=8.0 Hz, 1H), 7.65 (d, J=8.0 Hz, 2H), 7.62 (t, J=8.0 Hz, 1H), 7.53 (d, J=8.0 Hz, 2H), 7.38 (d, J=8.5 Hz, 1H), 7.29 (t, J=8.0 Hz, 1H), 6.00 (s, 1H), 4.89 (bs, 1H), 3.66 (s, 3H), 2.88 (m, 1H), 2.37 (m, 1H), 1.65-1.45 (m, 6H), 1.55 (s, 9H); LCMS (EI) m/z 494.0 (M$^+$), 495.1.

{1-[4-(1-Methyl-2-oxo-1,2-dihydro-quinolin-4-ylsulfanyl)-phenylcarbamoyl]-2-phenyl-ethyl}-carbamic acid tert-butyl ester

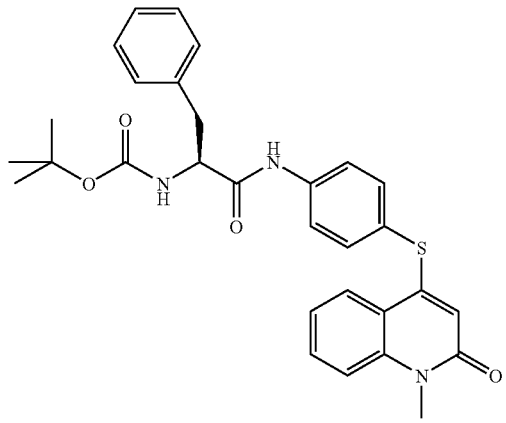

Yield: 80%. $^1$H NMR (500 MHz, CDCl$_3$) δ 8.31 (bs, 1H), 8.00 (d, J=8.0 Hz, 1H), 7.62 (t, J=8.0 Hz, 1H), 7.53 (d, J=8.0 Hz, 2H), 7.49 (d, J=8.0 Hz, 2H), 7.38 (d, J=8.5 Hz, 1H), 7.34-7.26 (m, 6H), 6.02 (s, 1H), 5.21 (bs, 1H), 4.53 (bs, 1H), 3.67 (s, 3H), 3.18 (m, 2H), 1.44 (s, 9H); LCMS (EI) m/z 530.0 (M$^+$), 531.0.

{2-(4-Methoxy-phenyl)-1-[4-(1-methyl-2-oxo-1,2-dihydro-quinolin-4-ylsulfanyl)-phenylcarbamoyl]-ethyl}-carbamic acid tert-butyl ester

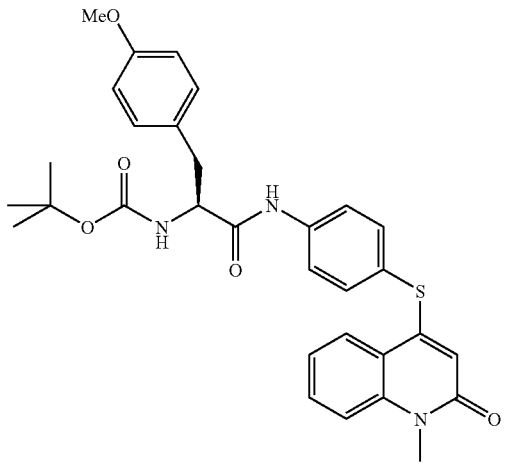

$^1$H NMR (500 MHz, CDCl$_3$) δ 8.25 (bs, 1H), 8.00 (d, J=8.0 Hz, 1H), 7.63 (t, J=8.0 Hz, 1H), 7.55 (d, J=8.0 Hz, 2H), 7.50 (d, J=8.0 Hz, 2H), 7.38 (d, J=8.5 Hz, 1H), 7.29 (t, J=8.0 Hz, 1H), 7.18 (d, J=8.0 Hz, 2H), 6.87 (d, J=8.0 Hz, 2H), 6.03 (s, 1H), 5.18 (bs, 1H), 4.46 (bs, 1H), 3.79 (s, 3H), 3.66 (s, 3H), 3.12 (d, J=7.0 Hz, 2H), 1.45 (s, 9H); LCMS (EI) m/z 560.0 (M$^+$), 561.1.

{2-(4-Fluoro-phenyl)-1-[4-(1-methyl-2-oxo-1,2-dihydro-quinolin-4-ylsulfanyl)-phenylcarbamoyl]-ethyl}-carbamic acid tert-butyl ester

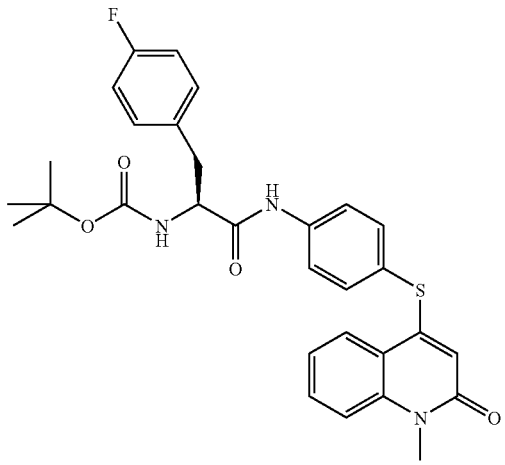

$^1$H NMR (500 MHz, CDCl$_3$) δ 8.43 (bs, 1H), 8.00 (d, J=8.0 Hz, 1H), 7.63 (t, J=8.0 Hz, 1H), 7.57 (d, J=8.0 Hz, 2H), 7.51 (d, J=8.0 Hz, 2H), 7.39 (d, J=8.5 Hz, 1H), 7.30 (t, J=8.0 Hz, 1H), 7.23 (m, 2H), 7.02 (m, 2H), 6.02 (s, 1H), 5.14 (bs, 1H), 4.48 (bs, 1H), 3.67 (s, 3H), 3.20 (dd, J=9.0, 7.0 Hz, 2H), 1.44 (s, 9H); LCMS (EI) m/z 548.0 (M$^+$), 549.0.

Example 13

HCV Replicon Luciferase Assay

Day 0, Cell Seeding and Compound Treatment: Huh-Luc-Neo Cells are seeded at 25,000/well in an opaque-walled 96 plate with Growth Medium (DMEM phenol red free+PS+2 mM glutamine; 100 μl/well). The compounds to be tested are added to the experimental wells (10 μl/well at 10× assay concentration) and the cells are then incubated (5% CO$_2$, 37° C.) for 48 h.

Day 2, Reagent Preparation and Luciferase Assay: The Bright-Glo Luciferase Assay Buffer (Promega) is thawed and equilibrated to room temperature prior to use. The lyophilized Bright-Glo Luciferase Assay Substrate is equilibrated to room temperature prior to use. 10 ml of Bright-Glo Luciferase Assay Buffer is transferred to 1 vial of Bright-Glo Luciferase Assay Substrate bottle and mixed by gently with a Vortex. 100 μl of Bright-Glo Luciferase Assay reagent (Bright-Glo Luciferase Assay Buffer+Bright-Glo Luciferase Assay Substrate Mixture) is added to each well. The well contents are mixed for 5 min. on an orbital shaker at room temperature to induce cell lysis and the luminescence is then measured using a luminometer. The data is analyzed and IC50s are determined using GraphPad Prism 4 software. Hits validated in the Replicon Luciferase assay have IC50s<8.0 μM and show <30% inhibition of Cell Viability at a compound concentration of 100 μM (Cell Titer Glow Assay, cell viability assay conditions identical to HCV Replicon Luciferase Assay conditions).

Example 14

HCV Replicon RNA Assay

Day 0, Cell Seeding and Compound Treatment: Huh-Luc-Neo Cells are seeded at 25,000/well in an opaque-walled 96 plate with Growth Medium (DMEM phenol red free+PS+2 mM glutamine; 100 μl/well). The compounds to be tested are added to the experimental wells (10 μl/well at 10× assay concentration) and the cells are then incubated (5% CO$_2$, 37° C.).

Day 1, Media Change and Compound Treatment: 24 hours after the initial compound treatment the cell culture media is aspirated from the wells and fresh Growth Medium is added (DMEM phenol red free+PS+2 mM glutamine; 100 μl/well). The compounds to be tested are then added to the appropriate experimental wells (10 μl/well at 10× assay concentration) and the cells are then incubated (5% CO2, 37° C.) for an additional 24 hrs.

Day 2, RNA Isolation and cDNA Synthesis: The cells are washed with 1× Phosphate Buffered Saline (PBS) once. Cells are then lysed and RNA is isolated in 96 well format using a vacuum manifold and the RNAeasy 96 kit (Qiagen) according to the manufacturer's suggested protocol. cDNA is then synthesized from RNA isolated from each well using the Taqman Reverse Transcription Reagents kit (Applied Biosystems) according to manufacturer's suggested protocol.

Day 3, Quantitative PCR Based Measurement of HCV RNA (Taqman Assay): Quantitative PCR analysis to measure HCV RNA expression from cDNA synthesized on Day 2 is performed using the ABI 9700 HT Sequence Detection System (Applied Biosystems) as previously described (Lohman et al, *Science* 285, 110-113, 1999). The data is analyzed and IC50s are determined using GraphPad Prism 4 software. Hits validated in the Replicon RNA Assay have IC50s<8.0 μM and show <30% inhibition of Cell Viability at a compound concentration of 50 μM (Cell Titer Glow Assay, cell viability assay conditions identical to HCV Replicon RNA Assay conditions).

Example 15

CellTiter-Glo Cell Viability Assay

Promega

Day 0, Cell Seeding and Compound Treatment: Huh-Luc-Neo Cells are seeded at 25,000/well in an opaque-walled 96 plate with Growth Medium (DMEM phenol red free+PS+2 mM glutamine; 100 ul/well). The compounds to be tested for inhibition of cell viability are added to the experimental wells (10 μl/well at 10× assay concentration) and the cells are then incubated (5% $CO_2$, 37° C.) for 48 h.

Day 2, Reagent Preparation and Assay: The CellTiter-Glo Buffer is thawed and equilibrated to room temperature prior to use. The lyophilized CellTiter-Glo Substrate is equilibrated to room temperature prior to use. 10 ml of CellTiter-Glo Buffer is transferred to 1 vial of CellTiter-Glo Substrate and mixed by gently with a Vortex. 100 μl of CellTiter-Glo Assay reagent (CellTiter-Glo Buffer+CellTiter-Glo Substrate Mixture) is added to each well. The well contents are mixed for 5 min. on an orbital shaker at room temperature to induce cell lysis and the luminescence is then measured using a luminometer.

The results of the Replicon Inhibition luciferase assay, the Replicon RNA (Taqman) assay, and the Cell viability assay are reported in Table 1. As there tends to be some variability in the data for RNA-based assays, the results are reported as ranges: A, $IC_{50}$>100 μM; B, $IC_{50}$=10-100 μM; C, $IC_{50}$=1-10 μM; D, $IC_{50}$<1 μM.

TABLE 1

| Comp. No. | Structure | Replicon Inhibition*, Luciferase | Replicon Inhibition*, Taqman | Cytotoxicity* |
|---|---|---|---|---|
| 001 | [4-bromophenylthio-substituted 1-methylquinolin-2(1H)-one] | C | D | A |
| 002 | [4-chlorophenylthio-substituted 1-methylquinolin-2(1H)-one] | C | C | A |
| 003 | [4-fluorophenylthio-substituted 1-methylquinolin-2(1H)-one] | C | C | A |

TABLE 1-continued

| Comp. No. | Structure | Replicon Inhibition*, Luciferase | Replicon Inhibition*, Taqman | Cytotoxicity* |
|---|---|---|---|---|
| 004 | 2,6-dichlorophenylthio-1-methylquinolin-2(1H)-one | C | D | A |
| 005 | 2-fluorophenylthio-1-methylquinolin-2(1H)-one | C | C | B |
| 006 | 2,5-dichlorophenylthio-1-methylquinolin-2(1H)-one | B | C | A |
| 007 | 3-fluorophenylthio-1-methylquinolin-2(1H)-one | C | C | A |
| 008 | 2-fluorophenylthio-1-methylquinolin-2(1H)-one | C | C | A |

TABLE 1-continued

| Comp. No. | Structure | Replicon Inhibition*, Luciferase | Replicon Inhibition*, Taqman | Cytotoxicity* |
|---|---|---|---|---|
| 009 | 4-(4-aminophenylthio)-1-methylquinolin-2(1H)-one | D | D | A |
| 010 | 4-(4-bromophenylthio)-1-ethylquinolin-2(1H)-one | C | D | A |
| 011 | 4-(4-bromophenylthio)-6-chloro-1-methylquinolin-2(1H)-one | C | C | A |
| 012 | 4-(4-methoxyphenylthio)-1-methylquinolin-2(1H)-one | C | B | A |
| 013 | 4-(4-tert-butylphenylthio)-1-methylquinolin-2(1H)-one | C | D | A |

TABLE 1-continued

| Comp. No. | Structure | Replicon Inhibition*, Luciferase | Replicon Inhibition*, Taqman | Cytotoxicity* |
|---|---|---|---|---|
| 014 | 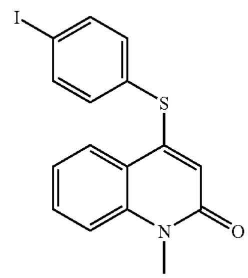 | C | D | A |
| 015 | 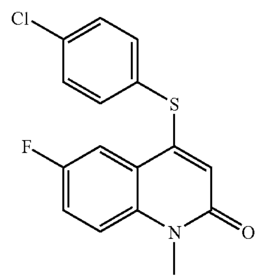 | C | C | A |
| 016 | 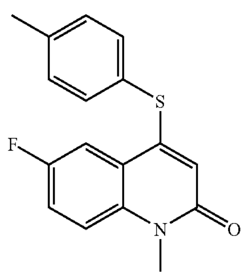 | C | C | A |
| 017 | 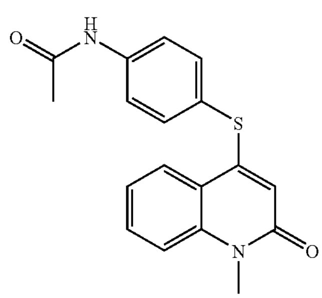 | C | C | A |
| 018 | 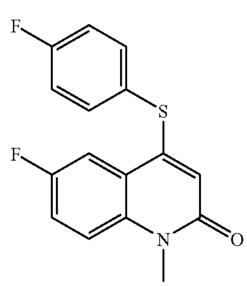 | C | C | A |

TABLE 1-continued

| Comp. No. | Structure | Replicon Inhibition*, Luciferase | Replicon Inhibition*, Taqman | Cytotoxicity* |
|---|---|---|---|---|
| 019 | 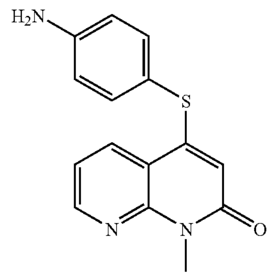 | D | C | A |
| 020 | 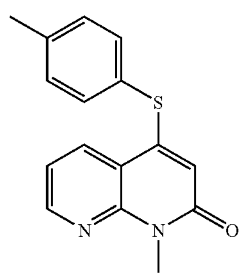 | D | C | A |
| 021 | 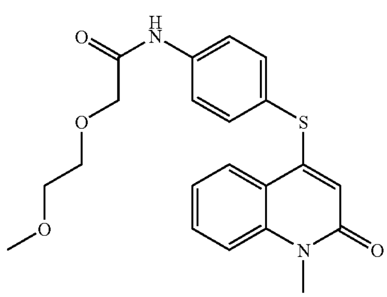 | D | C | A |
| 022 | 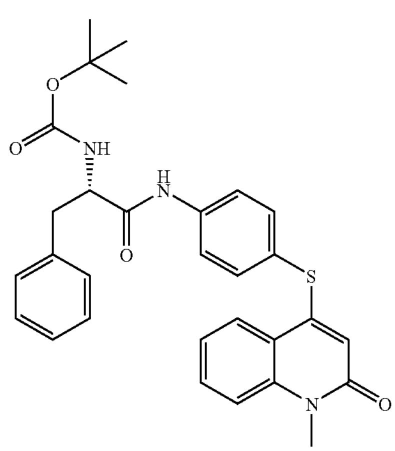 | C | C | A |

TABLE 1-continued
| Comp. No. | Structure | Replicon Inhibition*, Luciferase | Replicon Inhibition*, Taqman | Cytotoxicity* |
|---|---|---|---|---|
| 023 | 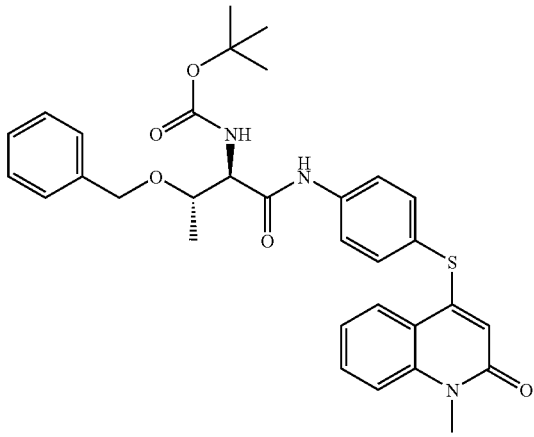 | C | C | A |
| 024 | 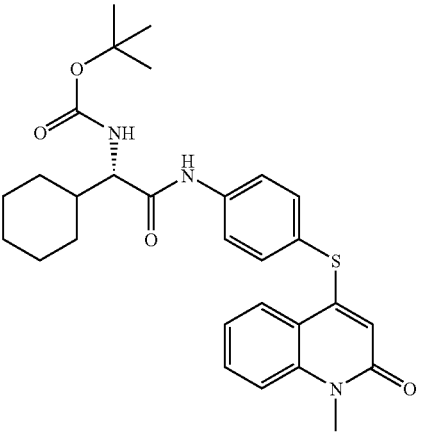 | D | C | A |
| 025 | 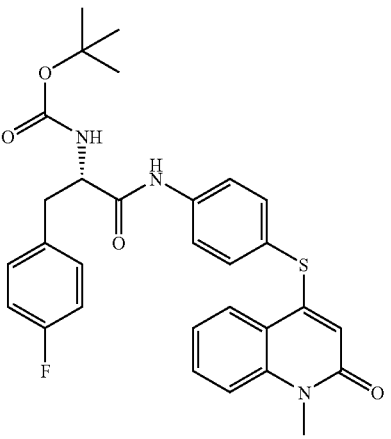 | C | C | A |

TABLE 1-continued

| Comp. No. | Structure | Replicon Inhibition*, Luciferase | Replicon Inhibition*, Taqman | Cytotoxicity* |
|---|---|---|---|---|
| 026 | 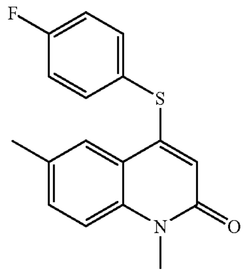 | D | D | B |
| 027 | 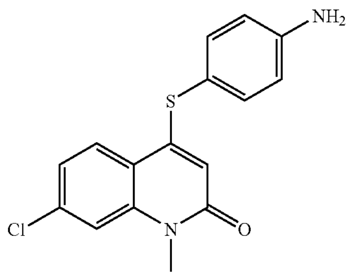 | D | D | B |
| 028 | 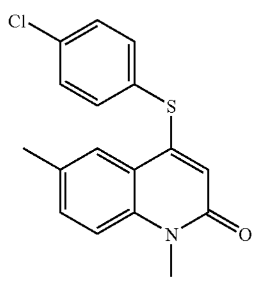 | D | D | B |
| 029 | 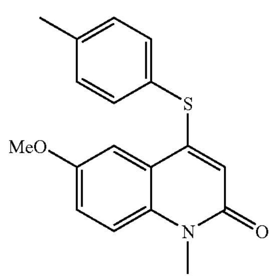 | D | D | A |
| 030 | 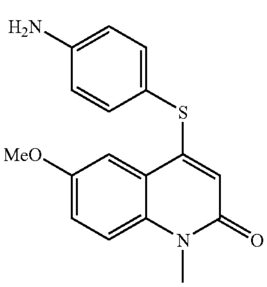 | D | D | B |

TABLE 1-continued

| Comp. No. | Structure | Replicon Inhibition*, Luciferase | Replicon Inhibition*, Taqman | Cytotoxicity* |
|---|---|---|---|---|
| 031 | 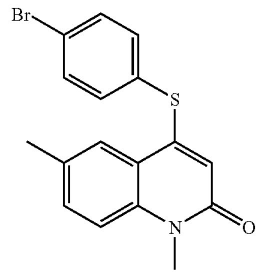 | D | D | B |
| 032 | 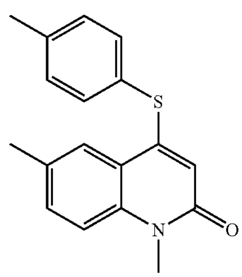 | D | D | B |
| 033 | 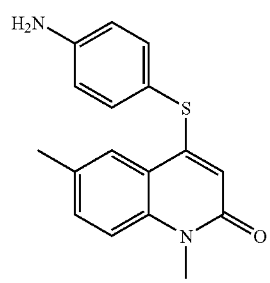 | D | D | A |
| 034 | 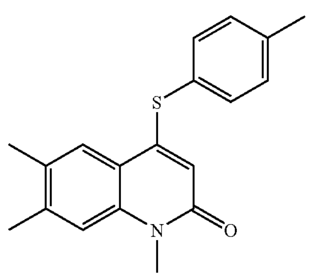 | D | D | A |
| 035 | 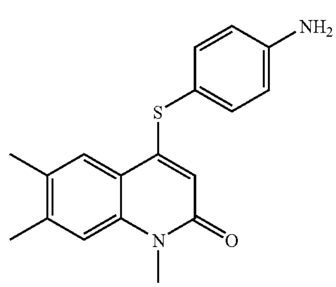 | D | D | A |

TABLE 1-continued

| Comp. No. | Structure | Replicon Inhibition*, Luciferase | Replicon Inhibition*, Taqman | Cytotoxicity* |
|---|---|---|---|---|
| 036 | 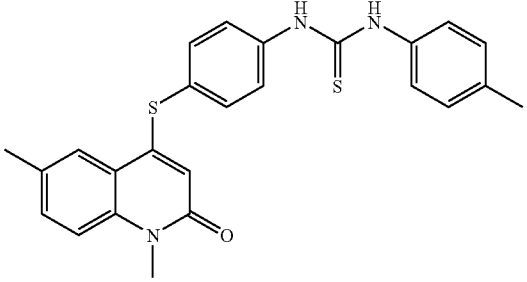 | C | C | A |
| 037 | 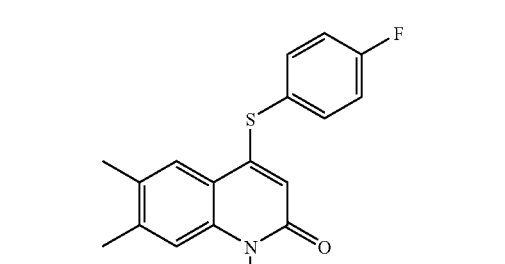 | D | D | A |
| 038 | 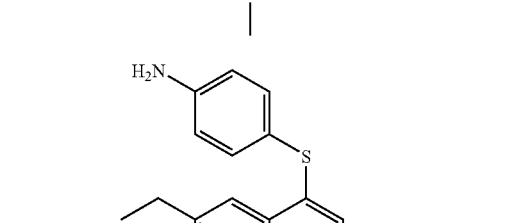 | D | D | A |

What is claimed is:

1. A compound of the formula II:

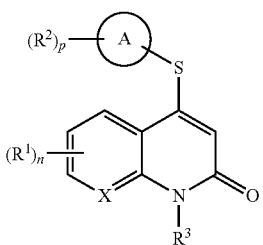

wherein:
X is C—H;
r is 0 to 6;
s is 0 to 6;
n is 0 to 3;
A is selected from an aryl group;
each $R^2$ is —$(CH_2)_v$—$N(R^{22})(R^{23})$ wherein:
  each $R^{22}$ and $R^{23}$ are independently selected from H, alkyl, cycloalkyl, cycloalkenyl, alkyl-O-alkyl, alkyl-O-aryl, alkenyl, alkynyl, aralkyl, aryl and a heterocyclic group; or $R^{22}$ and $R^{23}$ may be taken together with the nitrogen to which they are attached form a 5- to 7-membered ring which may optionally contain a further heteroatom and may be optionally substituted with up to three substituents selected from halo, CN, $NO_2$, alkyl, cycloalkyl, alkenyl, alkynyl, aralkyl, aryl, and a heterocyclic group;
v is 0 to 6;
p is 1
$R^3$ is selected from the group consisting of H, alkyl, cycloalkyl, alkenyl, alkynyl, aralkyl, aryl, a heterocyclic group, —$(CH_2)_xC(O)R^{31}$, —$(CH_2)_xC(O)N(R^{32})(R^{33})$, $(CH_2)_xC(O)OR^{31}$,
  $R^{31}$ is selected from H, alkyl, cycloalkyl, cycloalkenyl, alkenyl, alkynyl, aralkyl, aryl and
  a heterocyclic group;
  $R^{32}$ and $R^{33}$ are independently selected from H, alkyl, cycloalkyl, cycloalkenyl, alkenyl, alkynyl, aralkyl, aryl and a heterocyclic group;
  or $R^{32}$ and $R^{33}$ may be taken together with the nitrogen to which they are attached to form a 5- to 7-membered ring which may optionally contain a further heteroatom and may be optionally substituted with up to three substituents selected from halo, CN, $NO_2$, alkyl, cycloalkyl, alkenyl, alkynyl, aralkyl, aryl, and a heterocyclic group; and
x is 0 to 6;
or a pharmaceutically acceptable salt thereof.

2. The compound of claim 1 wherein A is phenyl.

3. The compound of claim 2, having the formula III$_a$:

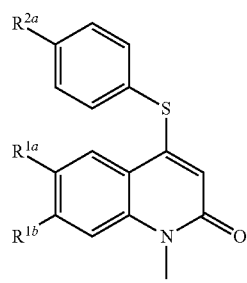

wherein:

R$^{1a}$ and R$^{1b}$ are independently selected from H, alkyl, alkenyl, alkynyl, aralkyl, —(CH$_2$)$_r$—O—R$^{11}$, —(CH$_2$)$_r$—N(R$^{12}$)(R$^{13}$)$_3$, —(CH$_2$)$_r$—N(R$^{11}$)—(CH$_2$)$_s$C(O)R$^{14}$, —(CH$_2$)$_r$, —N(R$^{11}$)SO$_2$R$^{11}$, —(CH$_2$)$_r$—SR$^{11}$, —(CH$_2$)$_r$—C(O)R$^{14}$, —(CH$_2$)$_r$—C(O)—(CH$_2$)$_s$OR$^{11}$, —(CH$_2$)$_r$—C(O)—(CH$_2$)$_s$N(R$^{12}$)(R$^{13}$), —(CH$_2$)$_r$O—(CH$_2$)$_s$—C(O)R$^{14}$, —(CH$_2$)$_r$OC(O)—(CH$_2$)$_s$N(R$^{12}$)(R$^{13}$), CN, CF$_3$, NO$_2$, SO$_2$, —SOR$^{11}$, —SO$_3$R$^{11}$, —SO$_2$N(R$^{12}$)(R$^{13}$), cycloalkyl, cycloalkenyl, halo, phosphate, phosphonate, aryl and a heterocyclic group;

each R$^{11}$ is independently selected from H, alkyl, alkyl-O-alkyl, alkyl-O-aryl, alkenyl, alkynyl, cycloalkyl, cycloalkenyl, aralkyl, aryl and a heterocyclic group;

each R$^{12}$ and R$^{13}$ are independently selected from H, alkyl, cycloalkyl, cycloalkenyl, alkyl-O-alkyl, alkyl-O-aryl, alkenyl, alkynyl, aralkyl, aryl and a heterocyclic group; or R$^{12}$ and R$^{13}$ may be taken together with the nitrogen to which they are attached form a 5- to 7-membered ring which may optionally contain a further heteroatom and may be optionally substituted with up to three substituents selected from halo, CN, NO$_2$, alkyl, cycloalkyl, alkenyl, alkynyl, aralkyl, aryl, and a heterocyclic group;

each R$^{14}$ is independently selected from H, alkyl, —OH, —O-alkyl, —O-aryl, —O-aralkyl, -alkyl-O-alkyl, -alkyl-O-aryl, alkenyl, alkynyl, cycloalkyl, cycloalkenyl, aralkyl, aryl and a heterocyclic group;

r is 0 to 6;

s is 0 to 6;

R$^{2a}$ is —(CH$_2$)$_v$—N(R$^{22}$)(R$^{23}$) wherein:

each R$^{22}$ and R$^{23}$ are independently selected from H, alkyl, cycloalkyl, cycloalkenyl, alkyl-O-alkyl, alkyl-O-aryl, alkenyl, alkynyl, aralkyl, aryl and a heterocyclic group; or R$^{22}$ and R$^{23}$ may be taken together with the nitrogen to which they are attached form a 5- to 7-membered ring which may optionally contain a further heteroatom and may be optionally substituted with up to three substituents selected from halo, CN, NO$_2$, alkyl, cycloalkyl, alkenyl, alkynyl, aralkyl, aryl, and a heterocyclic group;

v is 0 to 6; and p is 0 to 3.

4. The compound of claim 3, wherein R$^{1a}$ is selected from H, —NH$_2$, halo, alkyl, and —O-alkyl.

5. The compound of claim 1, having a chemical formula selected from:

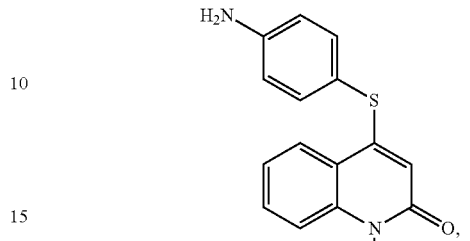

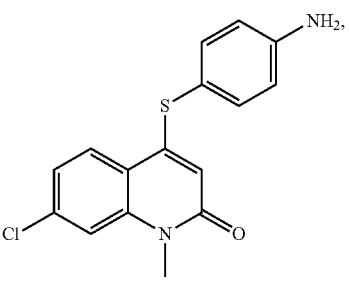

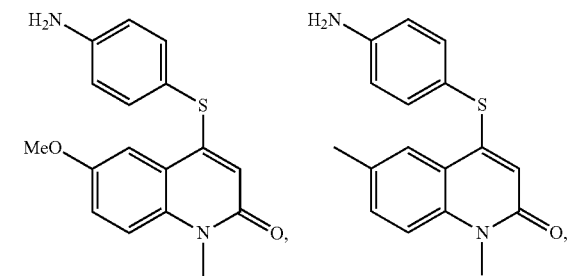

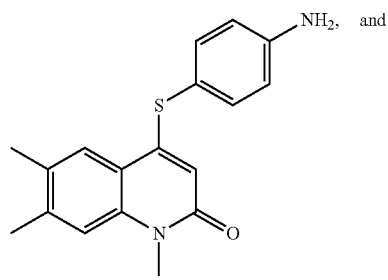

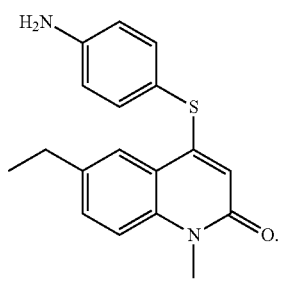

6. A method of treating infection with Hepatitis C virus comprising administering a pharmaceutically effective amount of a compound of the formula II:

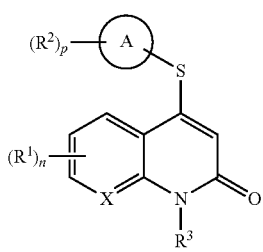

(II)

wherein:

X is C—H;

r is 0 to 6;

s is 0 to 6;

n is 0 to 3;

A is an aryl group;

each $R^2$ is —$(CH_2)_v$—$N(R^{22})(R^{23})$, wherein:

each $R^{22}$ and $R^{23}$ are independently selected from H, alkyl, cycloalkyl, cycloalkenyl, alkyl-O-alkyl, alkyl-O-aryl, alkenyl, alkynyl, aralkyl, aryl and a heterocyclic group; or $R^{22}$ and $R^{23}$ may be taken together with the nitrogen to which they are attached form a 5- to 7-membered ring which may optionally contain a further heteroatom and may be optionally substituted with up to three substituents selected from halo, CN, $NO_2$, alkyl, cycloalkyl, alkenyl, alkynyl, aralkyl, aryl, and a heterocyclic group;

v is 0 to 6;

p is 1; 0 to 3

$R^3$ is selected from the group consisting of H, alkyl, cycloalkyl, alkenyl, alkynyl, aralkyl, aryl, a heterocyclic group, —$(CH_2)_xC(O)R^{31}$, —$(CH_2)_xC(O)N(R^{32})(R^{33})$, and $(CH_2)_xC(O)OR^{31}$, $R^{31}$ is selected from H, alkyl, cycloalkyl, cycloalkenyl, alkenyl, alkynyl, aralkyl, aryl and a heterocyclic group;

$R^{32}$ and $R^{33}$ are independently selected from H, alkyl, cycloalkyl, cycloalkenyl, alkenyl, alkynyl, aralkyl, aryl and a heterocyclic group;

or $R^{32}$ and $R^{33}$ may be taken together with the nitrogen to which they are attached to form a 5- to 7-membered ring which may optionally contain a further heteroatom and may be optionally substituted with up to three substituents selected from halo, CN, $NO_2$, alkyl, cycloalkyl, alkenyl, alkynyl, aralkyl, aryl, and a heterocyclic group; and x is 0 to 6;

or a pharmaceutically acceptable salt or hydrate thereof.

7. The method of claim 6, wherein A is phenyl.

8. The method of claim 7, comprising administering a pharmaceutically effective amount of a compound of the formula $III_a$:

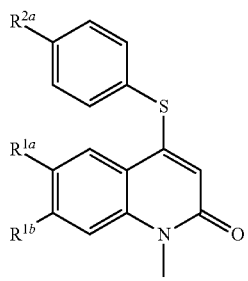

wherein:

$R^{1a}$ and $R^{1b}$ are independently selected from H, alkyl, alkenyl, alkynyl, aralkyl, —$(CH_2)_r$—O—$R^{11}$, —$(CH_2)_r$—$N(R^{12})(R^{13})$, —$(CH_2)_r$—$N(R^{11})$—$(CH_2)_s$$C(O)R^{14}$, —$(CH_2)_r$—$N(R^{11})SO_2R^{11}$, —$(CH_2)_r$—$SR^{11}$, —$(CH_2)_r$—$C(O)R^{14}$, —$(CH_2)_r$—$C(O)$—$(CH_2)_sOR^{11}$, —$(CH_2)_r$—$C(O)$—$(CH_2)_sN(R^{12})(R^{13})$, —$(CH_2)_r$O—$(CH_2)_s$—$C(O)R^{14}$, —$(CH_2)_rOC(O)$—$(CH_2)_sN(R^{12})(R^{13})$, CN, $CF_3$, $NO_2$, $SO_2$, —$SOR^{11}$, —$SO_3R^{11}$, —$SO_2N(R^{12})(R^{13})$, cycloalkyl, cycloalkenyl, halo, phosphate, phosphonate, aryl and a heterocyclic group;

each $R^{11}$ is independently selected from H, alkyl, alkyl-O-alkyl, alkyl-O-aryl, alkenyl, alkynyl, cycloalkyl, cycloalkenyl, aralkyl, aryl and a heterocyclic group;

each $R^{12}$ and $R^{13}$ are independently selected from H, alkyl, cycloalkyl, cycloalkenyl, alkyl-O-alkyl, alkyl-O-aryl, alkenyl, alkynyl, aralkyl, aryl and a heterocyclic group;

or $R^{12}$ and $R^{13}$ may be taken together with the nitrogen to which they are attached form a 5- to 7-membered ring which may optionally contain a further heteroatom and may be optionally substituted with up to three substituents selected from halo, CN, $NO_2$, alkyl, cycloalkyl, alkenyl, alkynyl, aralkyl, aryl, and a heterocyclic group;

each $R^{14}$ is independently selected from H, alkyl, —OH, —O-alkyl, —O-aryl, —O-aralkyl, -alkyl-O-alkyl, -alkyl-O-aryl, alkenyl, alkynyl, cycloalkyl, cycloalkenyl, aralkyl, aryl and a heterocyclic group;

r is 0 to 6;

s is 0 to 6;

$R^{2a}$ is —$(CH_2)_v$—$N(R^{22})(R^{23})$; wherein:

each $R^{22}$ and $R^{23}$ are independently selected from H, alkyl, cycloalkyl, cycloalkenyl, alkyl-O-alkyl, alkyl-O-aryl, alkenyl, alkynyl, aralkyl, aryl and a heterocyclic group; or $R^{22}$ and $R^{23}$ may be taken together with the nitrogen to which they are attached form a 5- to 7-membered ring which may optionally contain a further heteroatom and may be optionally substituted with up to three substituents selected from halo, CN, $NO_2$, alkyl, cycloalkyl, alkenyl, alkynyl, aralkyl, aryl, and a heterocyclic group;

v is 0 to 6;

p is 1.

9. The method of claim 8, wherein $R^{1a}$ and $R^{2a}$ are independently selected from H, —$NH_2$, halo, alkyl, and —O-alkyl, and $R^{2a}$ is selected from H and halo.

10. The method of claim 6, comprising administering a pharmaceutically effective amount of a compound having a chemical formula selected from:

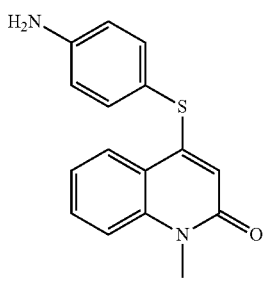

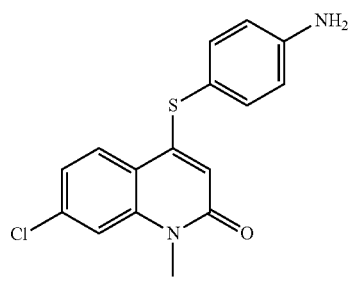

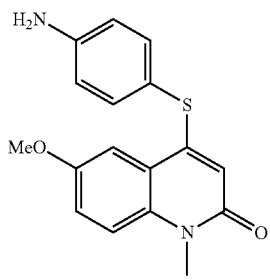 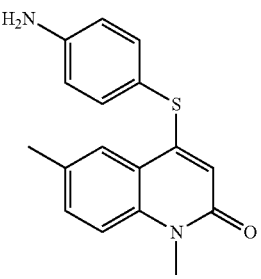

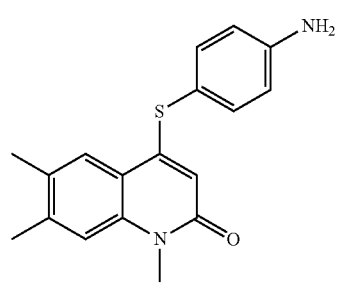

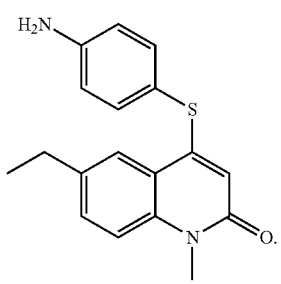

11. A compound of the formula II:

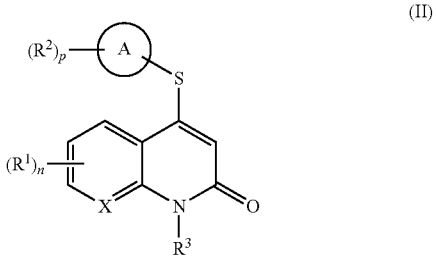

wherein:

X is C—$R^1$;

each $R^1$ is independently selected from alkyl, alkenyl, alkynyl, aralkyl, —$(CH_2)_rO$—$R^{11}$, —$(CH_2)_r$—$N(R^{12})(R^{13})$, —$(CH_2)_r$—$N(R^{11})$—$(CH_2)$., C(O)$R^{14}$, —$(CH_2)_r$—$N(R^{11})SO_2R^{11}$, —$(CH_2)_r$—$SR^{11}$, —$(CH_2)_r$—$C(O)R^{14}$, —$(CH_2)_rC(O)$—$(CH_2)_sOR^{11}$, —$(CH_2)_r$—$C(O)$—$(CH_2)_sN(R^{12})(R^{13})$, —$(CH_2)_rO$—$(CH_2)_s$—$C(O)R^{14}$, —$(CH_2)_rOC(O)$—$(CH_2)_sN(R^{12})(R^{13})$, CN, $CF_3$, $NO_2$, $SO_2$, —$SOR^{11}$, —$SO_3R^{11}$, —$SO_2N(R^{12})(R^{13})$, cycloalkyl, cycloalkenyl, halo, phosphate, phosphonate, aryl and a heterocyclic group;

each $R^{12}$ and $R^{13}$ are independently selected from H, alkyl, cycloalkyl, cycloalkenyl, alkyl-O-alkyl, alkyl-O-aryl, alkenyl, alkynyl, aralkyl, aryl and a heterocyclic group; or $R^{12}$ and $R^{13}$ may be taken together with the nitrogen to which they are attached form a 5- to 7-membered ring which may optionally contain a further heteroatom and may be optionally substituted with up to three substituents selected from halo, CN, $NO_2$, alkyl, cycloalkyl, alkenyl, alkynyl, aralkyl, aryl, and a heterocyclic group;

each $R^{14}$ is independently selected from H, alkyl, —OH, —O-alkyl, —O-aryl, —O-aralkyl, -alkyl-O-alkyl, -alkyl-O-aryl, alkenyl, alkynyl, cycloalkyl, cycloalkenyl, aralkyl, aryl and a heterocyclic group;

r is 0 to 6;

s is 0 to 6;

n is 0 to 3;

A is selected from an aryl group;

each $R^2$ is —$(CH_2)_v$—$N(R^{22})(R^{23})$ wherein:

each $R^{22}$ and $R^{23}$ are independently selected from H, alkyl, cycloalkyl, cycloalkenyl, alkyl-O-alkyl, alkyl-O-aryl, alkenyl, alkynyl, aralkyl, aryl and a heterocyclic group; or $R^{22}$ and $R^{23}$ may be taken together with the nitrogen to which they are attached form a 5- to 7-membered ring which may optionally contain a further heteroatom and may be optionally substituted with up to three substituents selected from halo, CN, $NO_2$, alkyl, cycloalkyl, alkenyl, alkynyl, aralkyl, aryl, and a heterocyclic group;

v is 0 to 6;

p is 1;

$R^3$ is selected from the group consisting of H, alkyl, cycloalkyl, alkenyl, alkynyl, aralkyl, aryl, a heterocyclic group, —$(CH_2)_xC(O)R^{31}$, —$(CH_2)_xC(O)N(R^{32})(R^{33})$, $(CH_2)_xC(O)OR^{31}$, $R^{31}$ is selected from H, alkyl, cycloalkyl, cycloalkenyl, alkenyl, alkynyl, aralkyl, aryl and a heterocyclic group;

$R^{32}$ and $R^{33}$ are independently selected from H, alkyl, cycloalkyl, cycloalkenyl, alkenyl, alkynyl, aralkyl, aryl and a heterocyclic group;
or $R^{32}$ and $R^{33}$ may be taken together with the nitrogen to which they are attached to form a 5- to 7-membered ring which may optionally contain a further heteroatom and may be optionally substituted with up to three substituents selected from halo, CN, $NO_2$, alkyl, cycloalkyl, alkenyl, alkynyl, aralkyl, aryl, and a heterocyclic group; and x is 0 to 6;

or a pharmaceutically acceptable salt thereof.

12. The compound of claim 11 wherein A is phenyl.

13. The compound of claim 12, having the formula $III_a$:

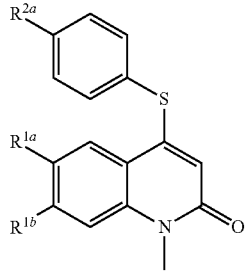

wherein:
$R^{1a}$ and $R^{1b}$ are independently selected from H, alkyl, alkenyl, alkynyl, aralkyl, $-(CH_2)_r-O-R^{11}$, $-(CH_2)_r-N(R^{12})(R^{13})$, $-(CH_2)_r-N(R^{11})-(CH_2)_sC(O)R^{14}$, $-(CH_2)_r-N(R^{11})SO_2R^{11}$, $-(CH_2)_r-SR^{11}$, $-(CH_2)_r-C(O)R^{14}$, $-(CH_2)_r-C(O)-(CH_2)_sOR^{11}$, $-(CH_2)_r-C(O)-(CH_2)_sN(R^{12})(R^{13})$, $-(CH_2)_rO-(CH_2)_s-C(O)R^{14}$, $-(CH_2)_rOC(O)-(CH_2)_sN(R^{12})(R^{13})$, CN, $CF_3$, $NO_2$, $SO_2$, $-SOR^{11}$, $-SO_3R^{11}$, $-SO_2N(R^{12})(R^{13})$, cycloalkyl, cycloalkenyl, halo, phosphate, phosphonate, aryl and a heterocyclic group;
each $R^{11}$ is independently selected from H, alkyl, alkyl-O-alkyl, alkyl-O-aryl, alkenyl, alkynyl, cycloalkyl, cycloalkenyl, aralkyl, aryl and a heterocyclic group;
each $R^{12}$ and $R^{13}$ are independently selected from H, alkyl, cycloalkyl, cycloalkenyl, alkyl-O-alkyl, alkyl-O-aryl, alkenyl, alkynyl, aralkyl, aryl and a heterocyclic group; or $R^{12}$ and $R^{13}$ may be taken together with the nitrogen to which they are attached form a 5- to 7-membered ring which may optionally contain a further heteroatom and may be optionally substituted with up to three substituents selected from halo, CN, $NO_2$, alkyl, cycloalkyl, alkenyl, alkynyl, aralkyl, aryl, and a heterocyclic group;
each $R^{14}$ is independently selected from H, alkyl, —OH, —O-alkyl, —O-aryl, —O-aralkyl, -alkyl-O-alkyl, -alkyl-O-aryl, alkenyl, alkynyl, cycloalkyl, cycloalkenyl, aralkyl, aryl and a heterocyclic group;
r is 0 to 6;
s is 0 to 6;
$R^{2a}$ is $-(CH_2)_v-N(R^{22})(R^{23})$ wherein:
each $R^{22}$ and $R^{23}$ are independently selected from H, alkyl, cycloalkyl, cycloalkenyl, alkyl-O-alkyl, alkyl-O-aryl, alkenyl, alkynyl, aralkyl, aryl and a heterocyclic group; or $R^{22}$ and $R^{23}$ may be taken together with the nitrogen to which they are attached form a 5- to 7-membered ring which may optionally contain a further heteroatom and may be optionally substituted with up to three substituents selected from halo, CN, $NO_2$, alkyl, cycloalkyl, alkenyl, alkynyl, aralkyl, aryl, and a heterocyclic group;
v is 0 to 6; and
p is 0 to 3.

14. The compound of claim 13, wherein $R^{1a}$ is selected from H, $-NH_2$, halo, alkyl, and —O-alkyl.

15. A method of treating infection with Hepatitis C virus comprising administering a pharmaceutically effective amount of a compound of the formula II:

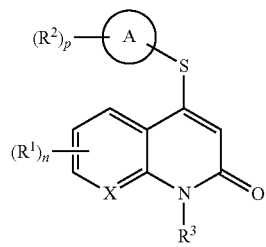

wherein:
X is C—$R^1$;
each $R^1$ is independently selected from alkyl, alkenyl, alkynyl, aralkyl, $-(CH_2)_r-O-R^{11}$, $-(CH_2)_r-N(R^{12})(R^{13})$, $-(CH_2)_r-N(R^{11})-(CH_2)_sC(O)R^{14}$, $-(CH_2)_r-N(R^{11})SO_2R^{11}$, $-(CH_2)_r-SR^{11}$, $-(CH_2)_r-C(O)R^{14}$, $-(CH_2)_r-C(O)-(CH_2)_sOR^{11}$, $-(CH_2)_r-C(O)-(CH_2)_sN(R^{12})(R^{13})_s-C(O)R^{14}$, $-(CH_2)_rOC(O)-(CH_2)_sN(R^{12})(R^{13})$, CN, $CF_3$, $NO_2$, $SO_2$, $-SOR^{11}$, $-SO_3R^{11}$, $-SO_2N(R^{12})(R^{13})$, cycloalkyl, cycloalkenyl, halo, phosphate, phosphonate, aryl and a heterocyclic group;
each $R^{12}$ and $R^{13}$ are independently selected from H, alkyl, cycloalkyl, cycloalkenyl, alkyl-O-alkyl, alkyl-O-aryl, alkenyl, alkynyl, aralkyl, aryl and a heterocyclic group; or $R^{12}$ and $R^{13}$ may be taken together with the nitrogen to which they are attached form a 5- to 7-membered ring which may optionally contain a further heteroatom and may be optionally substituted with up to three substituents selected from halo, CN, $NO_2$, alkyl, cycloalkyl, alkenyl, alkynyl, aralkyl, aryl, and a heterocyclic group;
each $R_{14}$ is independently selected from H, alkyl, —OH, —O-alkyl, —O-aryl, —O-aralkyl, -alkyl-O-alkyl, -alkyl-O-aryl, alkenyl, alkynyl, cycloalkyl, cycloalkenyl, aralkyl, aryl and a heterocyclic group;
r is 0 to 6;
s is 0 to 6;
n is 0 to 3;
A is an aryl group;
each $R^2$ is $-(CH_2)_v-N(R^{22})(R^{23})$, wherein:
each $R^{22}$ and $R^{23}$ are independently selected from H, alkyl, cycloalkyl, cycloalkenyl, alkyl-O-alkyl, alkyl-O-aryl, alkenyl, alkynyl, aralkyl, aryl and a heterocyclic group; or $R^{22}$ and $R^{23}$ may be taken together with the nitrogen to which they are attached form a 5- to 7-membered ring which may optionally contain a further heteroatom and may be optionally substituted with up to three substituents selected from halo, CN, $NO_2$, alkyl, cycloalkyl, alkenyl, alkynyl, aralkyl, aryl, and a heterocyclic group;
v is 0 to 6;
p is 1;

$R^3$ is selected from the group consisting of H, alkyl, cycloalkyl, alkenyl, alkynyl, aralkyl, aryl,
a heterocyclic group, —$(CH_2)_xC(O)R^{31}$, —$(CH_2)_xC(O)N(R^{32})(R^{33})$, and $(CH_2)_xC(O)OR^{31}$,
$R^{31}$ is selected from H, alkyl, cycloalkyl, cycloalkenyl, alkenyl, alkynyl, aralkyl, aryl and a heterocyclic group;
$R^{32}$ and $R^{33}$ are independently selected from H, alkyl, cycloalkyl, cycloalkenyl, alkenyl, alkynyl, aralkyl, aryl and a heterocyclic group;
 or $R^{32}$ and $R^{33}$ may be taken together with the nitrogen to which they are attached to form a 5- to 7-membered ring which may optionally contain a further heteroatom and may be optionally substituted with up to three substituents selected from halo, CN, $NO_2$, alkyl, cycloalkyl, alkenyl, alkynyl, aralkyl, aryl, and a heterocyclic group; and
x is 0 to 6;
or a pharmaceutically acceptable salt thereof.

16. The method of claim 15, wherein A is phenyl.

17. The method of claim 15, comprising administering a pharmaceutically effective amount of a compound of the formula $III_a$:

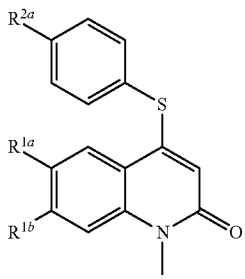

wherein:
$R^{1a}$ and $R^{1b}$ are independently selected from H, alkyl, alkenyl, alkynyl, aralkyl, —$(CH_2)_r$—O—$R^{11}$, —$(CH_2)_r$—$N(R^{12})(R^{13})$, —$(CH_2)_r$—$N(R^{11})$—$(CH_2)_sC(O)R^{14}$, —$(CH_2)_r$—$N(R^{11})SO_2R^{11}$, —$(CH_2)_r$—$SR^{11}$, —$(CH_2)_r$—$C(O)R^{14}$, —$(CH_2)_r$—$C(O)$—$(CH_2)_sOR^{11}$, —$(CH_2)_r$—$C(O)$—$(CH_2)_sN(R^{12})(R^{13})$, —$(CH_2)_r$—O—$(CH_2)_s$—$C(O)R^{14}$, —$(CH_2)_rOC(O)$—$(CH_2)_sN(R^{12})(R^{13})$, CN, $CF_3$, $NO_2$, $SO_2$, —$SOR^{11}$, —$SO_3R^{11}$, —$SO_2N(R^{12})(R^{13})$, cycloalkyl, cycloalkenyl, halo, phosphate, phosphonate, aryl and a heterocyclic group;
each $R^{11}$ is independently selected from H, alkyl, alkyl-O-alkyl, alkyl-O-aryl, alkenyl, alkynyl, cycloalkyl, cycloalkenyl, aralkyl, aryl and a heterocyclic group;
each $R^{12}$ and $R^{13}$ are independently selected from H, alkyl, cycloalkyl, cycloalkenyl, alkyl-O-alkyl, alkyl-O-aryl, alkenyl, alkynyl, aralkyl, aryl and a heterocyclic group;
 or $R^{12}$ and $R^{13}$ may be taken together with the nitrogen to which they are attached form a 5- to 7-membered ring which may optionally contain a further heteroatom and may be optionally substituted with up to three substituents selected from halo, CN, $NO_2$, alkyl, cycloalkyl, alkenyl, alkynyl, aralkyl, aryl, and a heterocyclic group;
each $R^{14}$ is independently selected from H, alkyl, —OH, —O-alkyl, —O-aryl, —O-aralkyl, -alkyl-O-alkyl, -alkyl-O-aryl, alkenyl, alkynyl, cycloalkyl, cycloalkenyl, aralkyl, aryl and a heterocyclic group;
r is 0 to 6;
s is 0 to 6;
$R^{2a}$ is —$(CH_2)_v$—$N(R^{22})(R^{23})$ wherein:
 each $R^{22}$ and $R^{23}$ are independently selected from H, alkyl, cycloalkyl, cycloalkenyl, alkyl-O-alkyl, alkyl-O-aryl, alkenyl, alkynyl, aralkyl, aryl and a heterocyclic group; or $R^{22}$ and $R^{23}$ may be taken together with the nitrogen to which they are attached form a 5- to 7-membered ring which may optionally contain a further heteroatom and may be optionally substituted with up to three substituents selected from halo, CN, $NO_2$, alkyl, cycloalkyl, alkenyl, alkynyl, aralkyl, aryl, and a heterocyclic group;
v is 0 to 6; and
p is 1.

18. The method of claim 15, wherein $R^{1a}$ and $R^{2a}$ are independently selected from H, —$NH_2$, halo, alkyl, and —O-alkyl, and $R^{2a}$ is selected from H and halo.

* * * * *

UNITED STATES PATENT AND TRADEMARK OFFICE
CERTIFICATE OF CORRECTION

PATENT NO.           : 8,143,276 B2  
APPLICATION NO.      : 11/895088  
DATED                : March 27, 2012  
INVENTOR(S)          : Zhen Yang et al.

Page 1 of 1

It is certified that error appears in the above-identified patent and that said Letters Patent is hereby corrected as shown below:

Column 59, line 67, after "they are attached," insert -- to --.

Column 60, line 47, after "p is 1," insert -- ; --.

Column 61, line 20, after "$N(R^{12})(R^{13})$," delete "$_3$".

Column 61, line 37, after "they are attached," insert -- to --.

Column 61, line 58, after "they are attached," insert -- to --.

Column 63, line 28, after "they are attached," insert -- to --.

Column 63, line 36, after "p is 1," delete "; 0 to 3".

Column 63, line 62, after "acceptable salt," delete "or hydrate".

Column 64, line 36, after "they are attached," insert -- to --.

Column 64, line 49, after "$R^{2a}$ is -," insert -- ( --.

Column 64, line 54, after "they are attached," insert -- to --.

Column 66, line 18, after "$(CH_2)_r$," insert -- - --.

Column 66, line 32, after "they are attached," insert -- to --.

Column 66, line 53, after "they are attached," insert -- to --.

Column 67, line 48, after "they are attached," insert -- to --.

Column 68, line 32, after "$N(R^{12})(R^{13})$," delete "$_s$-$C(O)R^{14}$".

Column 68, line 60, after "they are attached," insert -- to --.

Column 70, line 15, after "they are attached," insert -- to --.

Column 70, line 33, after "they are attached," insert -- to --.

Signed and Sealed this  
Twelfth Day of March, 2013

Teresa Stanek Rea  
*Acting Director of the United States Patent and Trademark Office*